US007189895B2

(12) United States Patent
McGonigle et al.

(10) Patent No.: US 7,189,895 B2
(45) Date of Patent: Mar. 13, 2007

(54) METHODS TO INCREASE THE ISOFLAVONOID LEVELS IN PLANTS AND PLANTS PRODUCING INCREASED LEVELS OF ISOFLAVONOIDS

(75) Inventors: Brian McGonigle, Wilmington, DE (US); Joan T. Odell, Unionville, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 430 days.

(21) Appl. No.: 10/459,159

(22) Filed: Jun. 11, 2003

(65) Prior Publication Data

US 2004/0006795 A1   Jan. 8, 2004

Related U.S. Application Data

(60) Provisional application No. 60/388,280, filed on Jun. 13, 2002.

(51) Int. Cl.
*C12N 15/29* (2006.01)
*C12N 15/52* (2006.01)
*C12N 15/82* (2006.01)
*A01H 5/00* (2006.01)
*A01H 5/10* (2006.01)

(52) U.S. Cl. .................. 800/312; 800/285; 800/286; 800/287; 800/298

(58) Field of Classification Search ................ 800/285, 800/286, 287, 298, 312
See application file for complete search history.

(56) References Cited

U.S. PATENT DOCUMENTS

| 3,488,770 | A | 1/1970 | Atkinson |
| 3,897,574 | A | 7/1975 | Pass |
| 4,454,804 | A | 6/1984 | McCulloch |
| 2003/0150012 | A1 | 8/2003 | Odell et al. |

FOREIGN PATENT DOCUMENTS

| WO | WO 99/37794 A1 | 7/1999 |
| WO | WO 99/43825 | 9/1999 |
| WO | WO 00/44909 A1 | 8/2000 |
| WO | WO 00/78979 A1 | 12/2000 |

OTHER PUBLICATIONS de Pater S. et al. Plant Molecular Biology, 1997; vol. 34, 169-174.*
Quattrocchio F. et al. The Plant Journal; 1998, vol. 13, No. 4 pp. 475-488.*
(Branch A.D. TIBS, Feb. 1998, pp. 45-50.*
Waterhouse P. et al., Trends in Plant Sciences, Nov. 1999, vol. 4, No. 11 pp. 452-457.*
Michael D. Purugganan et al., Molecular Evolution of the Plant R Regulatory Gene Family, Genetics, vol. 138:849-854, 1994.

Hiroshi Abe et al., Role of Arabidopsis MYC and MYB Homologs in Drought-and Abscisic Acid-Regulated Gene Expression, The Plant Cell, vol. 9:1859-1868, 1997.
Lodovico Tamagnone et al., The AmMyB308 and AmMyB330 Transcription Factors from Antirrhinum Regulate Phenylpropanoid and Lignin Biosynthesis in Transgenic Tobacco, The Plant Cell, vol. 10:135-154, 1998.
Chigen Tsukamoto et al., Factors Affecting Isoflavone Content in Soybean Seeds: Chagnes in Isoflavones, Saponins, and Composition of Fatty Acids at Different Temperatures during Seed Development, J. Agric. Food Chem., vol. 43:1184-1192, 1995.
Huei-Ju Wang et al., Isoflavone Composition of American and Japanese Soybeans in Iowa: Effects of Variety, Crop Year, and Location, J. Agric. Food Chem., vol. 42:1674-1677, 1994.
Richard A. Dixon et al., Stress-Induced Phenylpropanoid Metabolism, The Plant Cell, vol. 7:1085-1097, 1995.
Patricia A. Murphy et al., Isoflavones in Retail and Institutional Soy Foods, J. Agric. Food Chem., vol. 47:2697-2704, 1999.
Erich Grotewold et al., Engineering Secondary Metabolism in Maize Cells by Ectopic Expression of Transcription Factors, The Plant Cell, vol. 10:721-740, 1998.
Stephen A. Goff et al., Functional analysis of the transcriptional activator encoded by the maize B gene: evidence for a direct functional interaction between two classes of regulatory proteins, Genes & Development, vol. 6:864-875, 1992.
J. Pablo Radicella et al., Allelic diversity of the maize B regulatory gene: different leader and promoter sequences of two B alleles determine distinct tissue specificities of anthocyanin production, Genes & Development, vol. 6:2152-2164, 1992.
Elsbeth L. Walker et al., Transposon-mediated chromosomal rearrangements and gene duplications in the formation of the maize R-r complex, The EMBO Journal, vol. 14(10):2350-2363, 1995.
Wesley Bruce et al., Expression Profiling of the Maize Flavonoid Pathway Genes Controlled by Estradiol-Inducible Transcription Factors CRC and P, The Plant Cell, vol. 12:65-79, 2000.
Alan M. Lloyd et al., Anthocyanin Production Activated by Maize Regulators R and C1, Science, vol. 258:1773-1775, 1992.
Francesca Quattrocchio et al., Regulatory Genes Controlling Anthocyanin Pigmentation Are Functionally Conserved among Plant Species and Have Diistinct Sets of Target Genes, The Plant Cell, vol. 5:1497-1512, 1993.
John De Majnik et al., Transient expression of maize anthocyanin regulatory genes influences anthocyanin production in white clover and peas, Aust. J. Plant Phys., vol. 25:335-343, 1998.
M. F. Campbell et al., New Protein Foods, ed. by Altschul and Wilcke, Academic Press, vol. 5, Chapter 10, "Seed Storage Proteins", pp. 302-338, 1985.
Galen J. Rokey et al., Production of Pet Food, Feed Manufacturing Technology III, pp. 222-237, 1983.

(Continued)

*Primary Examiner*—Russell P. Kallis

(57) ABSTRACT

This invention pertains to methods of increasing isoflavonoid production in isoflavonoid-producing plants by transforming plants with at least one construct expressing at least a portion of a flavanone 3-hydroxylase, a C1 myb transcription factor, and an R-type myc transcription factor that regulate expression of genes in the phenylpropanoid pathway.

16 Claims, 10 Drawing Sheets

OTHER PUBLICATIONS

F. E. Horan, New Protein Foods, ed. by Altschul and Wilke, Academic Press, vol. 1A, Chapter 8, pp. 367-414, 1985.

M. Araba et al., Evaluation of Protein Solubility as an Indicator of Overprocessing Soybean Meal, Poultry Science, vol. 69:76-83, 1990.

* cited by examiner

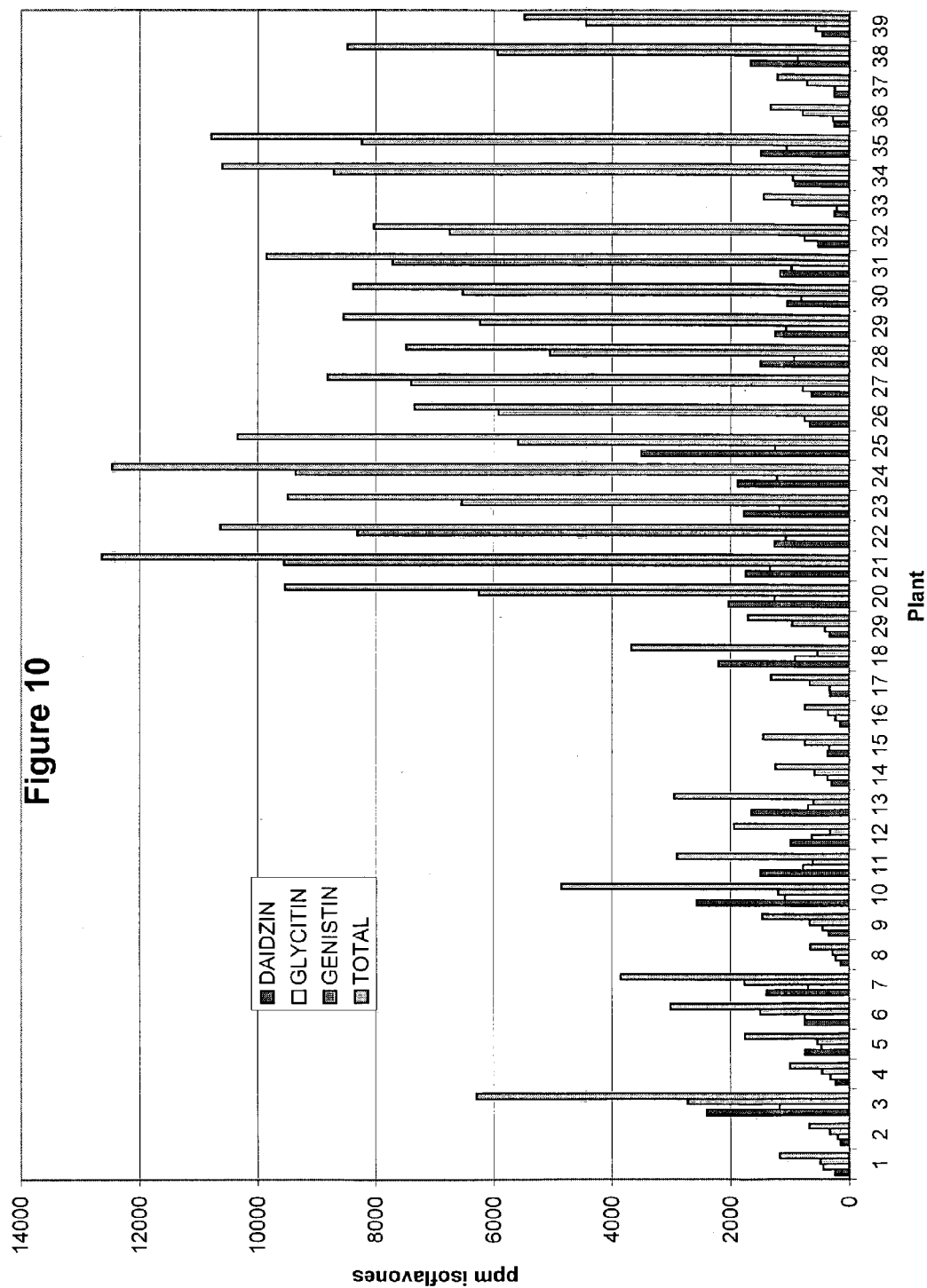

SEQUENCE LISTING

<160> NUMBER OF SEQ ID NOS: 10

<210> SEQ ID NO 1
<211> LENGTH: 7701
<212> TYPE: DNA
<213> ORGANISM: expression vector pKS151
<220> FEATURE:
<221> NAME/KEY: misc_feature
<222> LOCATION: (6516)..(6516)
<223> OTHER INFORMATION: n = A, C, G, or T

<400> SEQUENCE: 1

```
cgcgcccgat catccggata tagttcctcc tttcagcaaa aaaccccctca agacccgttt      60 agaggcccca agggggttatg ctagttattg ctcagcggtg gcagcagcca actcagcttc     120
ctttcgggct tgttagcag ccggatcgat ccaagctgta cctcactatt cctttgccct      180
cggacgagtg ctggggcgtc ggtttccact atcggcgagt acttctacac agccatcggt     240
ccagacggcc gcgcttctgc gggcgatttg tgtacgcccg acagtccggg ctccggatcg     300
gacgattgcg tcgcatcgac cctgcgccca agctgcatca tcgaaattgc cgtcaaccaa     360
gctctgatag agttggtcaa gaccaatgcg gagcatatac gcccggagcc gcggcgatcc     420
tgcaagctcc ggatgcctcc gctcgaagta gcgcgtctgc tgctccatac aagccaacca     480
cggcctccag aagaagatgt tggcgacctc gtattgggaa tccccgaaca tcgcctcgct     540
```

-continued

```
ccagtcaatg accgctgtta tgcggccatt gtccgtcagg acattgttgg agccgaaatc      600
cgcgtgcacg aggtgccgga cttcggggca gtcctcggcc caaagcatca gctcatcgag      660
agcctgcgcg acgacgcac tgacggtgtc gtccatcaca gtttgccagt gatacacatg       720
gggatcagca atcgcgcata tgaaatcacg ccatgtagtg tattgaccga ttccttgcgg      780
tccgaatggg ccgaacccgc tcgtctggct aagatcggcc gcagcgatcg catccatagc      840
ctccgcgacc ggctgcagaa cagcgggcag ttcggtttca ggcaggtctt gcaacgtgac      900
accctgtgca cggcgggaga tgcaataggt caggctctcg ctgaattccc caatgtcaag      960
cacttccgga atcgggagcg cggccgatgc aaagtgccga taaacataac gatctttgta     1020
gaaaccatcg gcgcagctat ttacccgcag gacatatcca cgccctccta catcgaagct     1080
gaaagcacga gattcttcgc cctccgagag ctgcatcagg tcggagacgc tgtcgaactt     1140
ttcgatcaga aacttctcga cagacgtcgc ggtgagttca ggcttttcca tgggtatatc     1200
tccttcttaa agtaaacaa aattatttct agagggaaac cgttgtggtc tccctatagt     1260
gagtcgtatt aatttcgcgg gatcgagatc gatccaattc caatcccaca aaaatctgag     1320
cttaacagca cagttgctcc tctcagagca gaatcgggta ttcaacaccc tcatatcaac     1380
tactacgttg tgtataacgg tccacatgcc ggtatatacg atgactgggg ttgtacaaag     1440
gcggcaacaa acggcgttcc cggagttgca cacaagaaat ttgccactat tacagaggca     1500
agagcagcag ctgacgcgta cacaacaagt cagcaaacag acaggttgaa cttcatcccc     1560
aaaggagaag ctcaactcaa gcccaagagc tttgctaagg ccctaacaag cccaccaaag     1620
caaaaagccc actggctcac gctaggaacc aaaaggccca gcagtgatcc agccccaaaa     1680
gagatctcct ttgccccgga gattacaatg gacgatttcc tctatcttta cgatctagga     1740
aggaagttcg aaggtgaagg tgacgacact atgttcacca ctgataatga aaggttagc      1800
ctcttcaatt tcagaaagaa tgctgaccca cagatggtta gagaggccta cgcagcaggt     1860
ctcatcaaga cgatctaccc gagtaacaat ctccaggaga tcaaatacct tcccaagaag     1920
gttaaagatg cagtcaaaag attcaggact aattgcatca agaacacaga gaaagacata     1980
tttctcaaga tcagaagtac tattccagta tggacgattc aaggcttgct tcataaacca     2040
aggcaagtaa tagagattgg agtctctaaa aaggtagttc ctactgaatc taaggccatg     2100
catggagtct aagattcaaa tcgaggatct aacagaactc gccgtgaaga ctggcgaaca     2160
gttcatacag agtcttttac gactcaatga caagaagaaa atcttcgtca acatggtgga     2220
gcacgacact ctggtctact ccaaaaatgt caaagataca gtctcagaag accaaagggc     2280
tattgagact tttcaacaaa ggataatttc gggaaacctc ctcggattcc attgcccagc     2340
tatctgtcac ttcatcgaaa ggacagtaga aaaggaaggt ggctcctaca atgccatca      2400
ttgcgataaa ggaaaggcta tcattcaaga tgcctctgcc gacagtggtc ccaaagatgg     2460
acccccaccc acgaggagca tcgtggaaaa agaagacgtt ccaaccacgt cttcaaagca     2520
agtggattga tgtgacatct ccactgacgt aagggatgac gcacaatccc actatccttc     2580
gcaagaccct tcctctatat aaggaagttc atttcatttg gagaggacac gctcgagctc     2640
atttctctat tacttcagcc ataacaaaag aactcttttc tcttcttatt aaaccatgaa     2700
aaagcctgaa ctcaccgcga cgtctgtcga agtttctg atcgaaaagt tcgacagcgt       2760
ctccgacctg atgcagctct cggagggcga agaatctcgt gctttcagct tcgatgtagg     2820
agggcgtgga tatgtcctgc gggtaaatag ctgcgccgat ggtttctaca agatcgtta     2880
tgtttatcgg cactttgcat cggccgcgct cccgattccg gaagtgcttg acattgggga     2940
```

```
attcagcgag agcctgacct attgcatctc ccgccgtgca cagggtgtca cgttgcaaga    3000
cctgcctgaa accgaactgc ccgctgttct gcagccggtc gcggaggcca tggatgcgat    3060
cgctgcggcc gatcttagcc agacgagcgg gttcggccca ttcgaccgc aaggaatcgg     3120
tcaatacact acatggcgtg atttcatatg cgcgattgct gatccccatg tgtatcactg    3180
gcaaactgtg atggacgaca ccgtcagtgc gtccgtcgcg caggctctcg atgagctgat    3240
gctttgggcc gaggactgcc ccgaagtccg gcacctcgtg cacgcggatt tcggctccaa    3300
caatgtcctg acgacaatg gccgcataac agcggtcatt gactgagcg aggcgatgtt      3360
cggggattcc caatacgagg tcgccaacat cttcttctgg aggccgtggt tggcttgtat    3420
ggagcagcag acgcgctact tcgagcggag gcatccggag cttgcaggat cgccgcggct    3480
ccgggcgtat atgctccgca ttggtcttga ccaactctat cagagcttgg ttgacggcaa    3540
tttcgatgat gcagcttggg cgcagggtcg atgcgacgca atcgtccgat ccggagccgg    3600
gactgtcggg cgtacacaaa tcgcccgcag aagcgcggcc gtctggaccg atggctgtgt    3660
agaagtactc gccgatagtg gaaaccgacg ccccagcact cgtccgaggg caaaggaata    3720
gtgaggtacc taagaagga gtgcgtcgaa gcagatcgtt caaacatttg gcaataaagt     3780
ttcttaagat tgaatcctgt tgccggtctt gcgatgatta tcatataatt tctgttgaat    3840
tacgttaagc atgtaataat taacatgtaa tgcatgacgt tatttatgag atgggttttt    3900
atgattagag tcccgcaatt atacatttaa tacgcgatag aaaacaaaat atagcgcgca    3960
aactaggata aattatcgcg cgcggtgtca tctatgttac tagatcgatg tcgaatctga    4020
tcaacctgca ttaatgaatc ggccaacgcg cggggagagg cggtttgcgt attgggcgct    4080
cttccgcttc ctcgctcact gactcgctgc gctcggtcgt tcggctgcgg cgagcggtat    4140
cagctcactc aaaggcggta atacggttat ccacagaatc aggggataac gcaggaaaga    4200
acatgtgagc aaaaggccag caaaaggcca ggaaccgtaa aaaggccgcg ttgctggcgt    4260
ttttccatag gctccgcccc cctgacgagc atcacaaaaa tcgacgctca agtcagaggt    4320
ggcgaaaccc gacaggacta taagatacc aggcgtttcc ccctggaagc tccctcgtgc     4380
gctctcctgt tccgaccctg ccgcttaccg gatacctgtc cgcctttctc ccttcgggaa    4440
gcgtggcgct ttctcaatgc tcacgctgta ggtatctcag ttcggtgtag tcgttcgct     4500
ccaagctggg ctgtgtgcac gaaccccccg ttcagcccga ccgctgcgcc ttatccggta    4560
actatcgtct tgagtccaac ccggtaagac acgacttatc gccactggca gcagccactg    4620
gtaacaggat tagcagagcg aggtatgtag gcggtgctac agagttcttg aagtggtggc    4680
ctaactacgg ctacactaga aggacagtat ttggtatctg cgctctgctg aagccagtta    4740
ccttcggaaa aagagttggt agctcttgat ccggcaaaca accaccgct ggtagcggtg     4800
gttttttgt ttgcaagcag cagattacgc gcagaaaaaa aggatctcaa gaagatcctt     4860
tgatcttttc tacggggtct gacgctcagt ggaacgaaaa ctcacgttaa gggattttgg    4920
tcatgacatt aacctataaa aataggcgta tcacgaggcc ctttcgtctc gcgcgtttcg    4980
gtgatgacgg tgaaaacctc tgacacatgc agctcccgga gacggtcaca gcttgtctgt    5040
aagcggatgc cgggagcaga caagcccgtc agggcgcgtc agcgggtgtt ggcgggtgtc    5100
ggggctggct taactatgcg gcatcagagc agattgtact gagagtgcac catatggaca    5160
tattgtcgtt agaacgcggc tacaattaat acataacctt atgtatcata cacatacgat    5220
ttaggtgaca ctatagaacg gcgcgccgtc gacggatata atgagccgta aacaaagatg    5280
```

```
attaagtagt aattaatacg tactagtaaa agtggcaaaa gataacgaga aagaaccaat     5340
ttctttgcat tcggccttag cggaaggcat atataagctt tgattatttt atttagtgta     5400
atgatttcgt acaaccaaag catttattta gtactctcac acttgtgtcg cggccggagc     5460
tggtcatctc gctcatcgtc gagtcggcgg ccggagctgg tcatctcgct catcgtcgag     5520
tcggcggccg ccgactcgac gatgagcgag atgaccagct ccggccgccg actcgacgat     5580
gagcgagatg accagctccg gccgcttggg gggctatgga agactttctt agttagttgt     5640
gtgaataagc aatgttggga gaatcgggac tacttatagg ataggaataa aacagaaaag     5700
tattaagtgc taatgaaata tttagactga taattaaaat cttcacgtat gtccacttga     5760
tataaaaacg tcaggaataa aggaagtaca gtagaattta aggtactctc ttttatatat     5820
acccgtgttc tcttttggc tagctagttg cataaaaaat aatctatatt tttatcatta      5880
ttttaaatat cttatgagat ggtaaatatt tatcataatt tttttacta ttatttatta     5940 tttgtgtgtg taatacatat agaagttaat tacaaattt atttacttt tcattatttt      6000 gatatgattc accattaatt tagtgttatt atttataata gttcatttta atcttttgt     6060 atatattatg cgtgcagtac ttttttccta catataacta ctattacatt ttatttatat    6120 aatatttta ttaatgaatt ttcgtgataa tatgtaatat tgttcattat tatttcagat    6180
tttttaaaaa tatttgtgtt attatttatg aaatatgtaa ttttttagt atttgatttt    6240 atgatgataa agtgttctaa attcaaaaga agggggaaag cgtaaacatt aaaaaacgtc     6300
atcaaacaaa aacaaaatct tgttaataaa gataaaactg tttgttttga tcactgttat    6360
ttcgtaatat aaaaacatta tttatattta tattgttgac aaccaaattt gcctatcaaa    6420
tctaaccaat ataatgcatg cgtggcaggt aatgtactac catgaactta agtcatgaca    6480
taataaaccg tgaatctgac caatgcatgt acctanctaa attgtatttg tgacacgaag    6540
caaatgattc aattcacaat ggagatggga acaaataat gaagaaccca gaactaagaa     6600
agcttttctg aaaaataaaa taaaggcaat gtcaaaagta tactgcatca tcagtccaga    6660
aagcacatga tattttttta tcagtatcaa tgcagctagt tttatttac aatatcgata     6720 tagctagttt aaatatattg cagctagatt tataaatatt tgtgttatta tttatcattt    6780
gtgtaatcct gttttagta ttttagttta tatgatga taatgtattc caaatttaaa      6840
agaagggaaa taaatttaaa caagaaaaaa agtcatcaaa caaaaaacaa atgaaagggt    6900
ggaaagatgt taccatgtaa tgtgaatgtt acagtatttc ttttattata gagttaacaa    6960
attaactaat atgattttgt taataatgat aaaatatttt tttattatt atttcataat    7020 ataaaaatag tttacttaat ataaaaaaaa ttctatcgtt cacaacaaag ttggccacct    7080
aatttaacca tgcatgtacc catggaccat attaggtaac catcaaacct gatgaagaga    7140
taaagagatg aagacttaag tcataacaca aaaccataaa aaacaaaaat acaatcaacc    7200
gtcaatctga ccaatgcatg aaaaagctgc aatagtgagt ggcgacacaa agcacatgat    7260
tttcttacaa cggagataaa accaaaaaaa tatttcatga acaacctaga acaaataaag    7320
cttttatata ataaatatat aaataaataa aggctatgga ataatatact tcaatatatt    7380
tggattaaat aaattgttgg cggggttgat atatttatac acacctaaag tcacttcaat    7440 ctcatttca cttaactttt attttttttt tcttttatt tatcataaag agaatattga      7500
taatatactt tttaacatat ttttatgaca ttttttattg gtgaaaactt attaaaaatc    7560
ataaattttg taagttagat ttatttaaag agttcctctt cttattttaa atttttaat     7620 aaattttaa ataactaaaa tttgtgttaa aaatgttaaa aaatgtgtta ttaaccctttc    7680
```

-continued

```
tcttcgagga tccaagcttg g                                              7701

<210> SEQ ID NO 2
<211> LENGTH: 26
<212> TYPE: DNA
<213> ORGANISM: Amplification Primer sense

<400> SEQUENCE: 2
gcggccgcat ggcaccaaca gccaag                                         26

<210> SEQ ID NO 3
<211> LENGTH: 26
<212> TYPE: DNA
<213> ORGANISM: Amplification primer antisense

<400> SEQUENCE: 3
gcggccgcat ccgtgtggcg cttcag                                         26

<210> SEQ ID NO 4
<211> LENGTH: 1465
<212> TYPE: DNA
<213> ORGANISM: Glycine max

<400> SEQUENCE: 4
gcacgagggc acgaggaagc attgcattct gctatttaat tccactacgt acacgcacat    60
tctcctcaaa gacaacaatg gcaccaacag ccaagactct gacttacctg cccaggaga    120
aaacccctaga atcgagcttc gttcgggacg aggaggagcg tcccaaggtt gcctacaacg   180
aattcagcga cgagatccca gtgatttctc ttgccggaat cgacgaggtg gatggacgca    240
gaagagagat ttgtgagaag atcgtggagg cttgcgagaa ttggggtata ttccaggttg    300
ttgatcacgg tgtggatcaa caactcgtgg ccgagatgac ccgtctcgcc aaagagttct    360
ttgctttgcc accggacgag aagcttcgtt ttgatatgtc cggcgccaaa aagggtggat    420
tcattgtctc cagccatctc aaggggaat cggtgcagga ctggagagaa atagtgacat     480
acttttcgta cccaaaaaga gagggact attcaaggtg gccagacacg ccagaaggg t     540
ggagatcggt gactgaggaa tacagcgaca agtaatgggt ctagcttgc aagctcatgg     600
aggtgttgtc cgaagcaatg gggttagaga agagggtttt aagcaaagca tgtgttgaca    660
tggaccagaa ggtggtggtt aattactacc ccaaatgccc tcaacctgac ctcactcttg    720
gcctgaagcg ccacacggat ccgggcacta tcacccttgct gcttcaggac caagtgggtg    780
gacttcaagc caccagggac aatggcaaaa catggatcac cgttcagcct gtggaggctg    840
cccttcgtcgt caatcttgga gatcatgctc attatctgag caatggaagg ttcaagaatg    900
ctgatcacca agcggtggtg aactcaaacc atagccgttt gtccatagcc acttttcaaa    960
acccagcacc aaatgcaact gtttaccctc tgaagataag agaaggagag aagcctgtga   1020
tggaggaacc aatcactttt gctgaaatgt acaggaggaa gatgagcaag acattgaga   1080
ttgcaaggat gaagaagctg gctaaggaaa gcatttgca ggaccttgag aatgaaaagc    1140
atttgcaaga acttgatcag aaggcaaaac ttgaggccaa gcctttgaag gagattcttg   1200
cttaattaat aataattaca tatgtatcat ttgcatgccc ccttggtgtt tttagtattt    1260
tttaagggcc atgaattaat aatagtcctt acctttgtgc ttttgtacgt cttatgattt   1320
atcctttgtg gggatatcat gtgttgtgtt cagttgccta tgtcttatta gctagctggc    1380
tcatctatgt ataccttata tgtgcctcta ttataaatga aaataagtgg cactgtcttt   1440
```

-continued

```
attaaaaaaa aaaaaaaaaa aaaaa                                    1465

<210> SEQ ID NO 5
<211> LENGTH: 23
<212> TYPE: DNA
<213> ORGANISM: Amplification primer3

<400> SEQUENCE: 5
tcctcagtca ccgatctcca ccc                                       23

<210> SEQ ID NO 6
<211> LENGTH: 22
<212> TYPE: DNA
<213> ORGANISM: Amplification Primer4

<400> SEQUENCE: 6
cggatataat gagccgtaaa ca                                        22

<210> SEQ ID NO 7
<211> LENGTH: 25
<212> TYPE: DNA
<213> ORGANISM: Amplification primer5

<400> SEQUENCE: 7
tggatggacg cagaagagag atttg                                     25

<210> SEQ ID NO 8
<211> LENGTH: 25
<212> TYPE: DNA
<213> ORGANISM: Amplification primer6

<400> SEQUENCE: 8
ccgattctcc caacattgct tattc                                     25

<210> SEQ ID NO 9
<211> LENGTH: 22
<212> TYPE: DNA
<213> ORGANISM: Amplification primer1

<400> SEQUENCE: 9
aggcggaaga actgctgcaa cg                                        22

<210> SEQ ID NO 10
<211> LENGTH: 22
<212> TYPE: DNA
<213> ORGANISM: Amplification primer2

<400> SEQUENCE: 10
aggtccattt cgtcgcagag gc                                        22
```

METHODS TO INCREASE THE ISOFLAVONOID LEVELS IN PLANTS AND PLANTS PRODUCING INCREASED LEVELS OF ISOFLAVONOIDS

This application claims the benefit of U.S. Provisional Application No. 60/388,280, filed 13 Jun. 2002. The entire content of this provisional application is herein incorporated by reference.

This invention pertains to methods of increasing isoflavonoid production in isoflavonoid-producing plants by transforming plants with at least one construct comprising nucleic acid fragments encoding at least a portion of a flavanone 3-hydroxylase, a C1 myb transcription factor, and an R-type myc transcription factor.

Isoflavonoids represent a class of secondary metabolites produced in legumes by a branch of the phenylpropanoid pathway and include such compounds as isoflavones, isoflavanones, rotenoids, pterocarpans, isoflavans, quinone derivatives, 3-aryl-4-hydroxycoumarins, 3-arylcoumarins, isoflav-3-enes, coumestans, alpha-methyldeoxybenzoins, 2-arylbenzofurans, isoflavanol, coumaronochromone and the like. In plants, these compounds are known to be involved in interactions with other organisms and to participate in the defense responses of legumes against phytopathogenic microorganisms (Dewick, P. M. (1993) in The Flavonoids, Advances in Research Since 1986, Harborne, J. B. Ed., pp. 117–238, Chapman and Hall, London). Isoflavonoid-derived compounds also are involved in symbiotic relationships between roots and rhizobial bacteria which eventually result in nodulation and nitrogen-fixation (Phillips, D. A. (1992) in *Recent Advances in Phytochemistry*. Vol. 26, pp 201–231, Stafford, H. A. and Ibrahim, R. K., Eds, Plenum Press, New York), and overall they have been shown to act as antibiotics, repellents, attractants, and signal compounds (Barz, W. and Welle, R. (1992) *Phenolic Metabolism in Plants*, pg 139–164, Ed by H. A. Stafford and R. K. Ibrahim, Plenum Press, New York).

Isoflavonoids have also been reported to have physiological activity in animal and human studies. For example, it has been reported that the isoflavones found in soybean seeds possess antihemolytic (Naim, M., et al. (1976) *J. Agric. Food Chem*. 24:1174–1177), antifungal (Naim, M., et al. (1974) *J. Agr. Food Chem*. 22:806–810), estrogenic (Price, K. R. and Fenwick, G. R. (1985) *Food Addit. Contam*. 2:73–106), tumor-suppressing (Messina, M. and Barnes, S. (1991) *J. Natl. Cancer Inst*. 83:541–546; Peterson, G., et al. (1991) *Biochem. Biophys. Res. Commun*. 179:661–667), hypolipidemic (Mathur, K., et. al. (1964) *J. Nutr*. 84:201–204), and serum cholesterol-lowering (Sharma, R. D. (1979) *Lipids* 14:535–540) effects. In addition, both epidemiological and dietary-intervention studies indicate that when isoflavones in soybean seeds and in subsequent protein products prepared from the seeds are part of the human dietary intake, those products provide many significant health benefits (Messina, M. J. (1999) *Am. J. Clin. Nutr*. 70:439S–450S).

Free isoflavones rarely accumulate to high levels in soybeans. Instead they are usually conjugated to carbohydrates or organic acids. Soybean seeds contain three types of isoflavones aglycones, glucosides, and malonylglucosides. Each isoflavone type is found in three different forms: daidzein, genistein, and glycitein form the aglycones; daidzin, genistin, and glycitin form the glucosides; and 6"-O-malonyldaidzin, 6"-O-malonylgenistin and 6"-O-malonyllycitin form the malonylglucosides. During processing acetylglucoside forms are produced: 6'-O-acetyldaidzin, 6'-O-acetyl genistin, and 6'-O-acetyl glycitin. The content of isoflavonoids in soybean seeds is quite variable and is affected by both genetics and environmental conditions such as growing location and temperature during seed fill (Tsukamoto, C., et al. (1995) *J. Agric. Food Chem*. 43:1184–1192; Wang, H. and Murphy, P. A. (1994) *J. Agric. Food Chem*. 42:1674–1677). In addition, isoflavonoid content in legumes can be stress-induced by pathogen attack, wounding, high UV light exposure and pollution (Dixon, R. A. and Paiva, N. L. (1995) *Plant Cell* 7:1085–1097). The genistein isoflavonoid forms make up the most abundant group in soybean seeds and most food products, while the daidzein and the glycitein forms are present in lower levels (Murphy, P. A. (1999) *J. Agric. Food Chem*. 47:2697–2704).

The biosynthetic pathway for isoflavonoids in soybean and their relationship with several other classes of phenylpropanoids is presented in FIG. 1. The enzyme flavanone 3-hydroxylase (F3H; EC 1.14.11.9) catalyzes the conversion of flavanones to dihydroflavonols, which are intermediates in the biosynthesis of flavonols, anthocyanidins, catechins and proanthocyanidins. This enzyme is also referred to as naringenin 3-dioxygenase, and naringenin, 2-oxoglutarate 3-dioxygenase, among others. In soybean, both flavanone 3-hydroxylase and isoflavone synthase (IFS) compete for naringenin as a substrate and it is not clear how this competition is regulated. Suppression of F3H has been shown to increase the resistance of cultivated plants to chemical stress (PCT publication WO 00/78979, published Dec. 28, 2000).

Though the branch initiated by isoflavone synthase that leads to synthesis of isoflavonoids is mainly limited to the legumes, the remainder of the phenylpropanoid pathway occurs in other plant species. In *maize*, genes of the phenylpropanoid pathway are regulated by the transcription factor C1 in combination with an R-type factor. Together C1 and an R-type factor activate expression of a set of genes that leads to the synthesis and accumulation of anthocyanins in *maize* cells (Grotewold, E., et al. (1998) *Plant Cell* 10:721–740).

*Maize* C1 is a myb-type transcription factor that regulates expression of genes involved in anthocyanin production and accumulation in *maize* cells. However C1 cannot activate gene expression alone, and requires interaction with an R-type myc transcription factor for activation of target gene promoters. The R-type factors include, among others, alleles of R, alleles of the homologous B gene of *maize*, and alleles of the homologous Lc gene. These genes function similarly and make up the R/B gene family (Goff, S. A., et al. (1992) *Genes Dev*. 6:864–875). The various genes of the R/B gene family may be in turn each found as diverging alleles that fluctuate in expression pattern within the corn plant due to differences in their promoters. The members of this family encode proteins with very similar amino acid sequences and thus have comparable effects on the anthocyanin pathway structural genes. The specificity of the different promoters provides tissue specificity of anthocyanin biosynthesis (Radicella, J. P. et al. (1992) *Genes Dev*. 6:2152–2164; Walker, E. L. (1995) *EMBO J*. 14:2350–2363). The skilled artisan will recognize that the coding region of any functional gene of this large family could be used in conjunction with a promoter of choice to obtain R-gene function in the desired tissue or developmental stage. Examples of R/B family genes and alleles include, but are not limited to, Lc, R, R-S, R-P, Sn, B-Peru, and B-I. The coding regions of particular alleles of the Lc or B genes, especially the B-Peru allele, have been most commonly used in experiments in conjunction with C1.

Cell suspension lines of the *maize* inbred Black Mexican Sweet (BMS) that were transformed with an estradiol-inducible version of a fusion of C1 and R (CRC) were analyzed after the addition of estradiol. The cDNA fragments from the known flavonoid genes, except chalcone isomerase, were induced in the CRC-expressing line after hormone induction (Bruce et al. (2000) *Plant Cell* 12:65–80). *Maize* C1 and an R-type factor together can promote the synthesis of anthocyanins in Arabidopsis tissues that do not naturally express anthocyanins (Lloyd, A. M., et al. (1992) *Science* 258:1773–1775), and in petunia leaves (Quattrocchio, F., et al. (1993) *Plant Cell* 5:1497–1512). WO 99/37794, published Jul. 29, 1999, discloses that the expression of *maize* C1 and the Lc allele of R in tomato fruit results in increased levels of the flavonol kaempferol. Thus, it is known that C1 and an R-type factor can regulate expression of individual genes of the phenylpropanoid pathway in plants including Arabidopsis, petunia, tomato, and *maize* leading to production of anthocyanins or flavonols. These are all plants that do not produce isoflavonoids. Isoflavonoid production is almost exclusively limited to the legumes. An example of one of the few non-legume plants that does produce isoflavonoids is sugar beet.

WO 00/44909, published Aug. 3, 2000, discloses transformation of soybeans with *maize* C1 and R (as a CRC chimera) in conjunction with overexpression of the isoflavone synthase gene. Visual inspection, after transient expression of C1 and B-Peru in white clover and pea, which are legumes, shows production of anthocyanin in several tissues (Majnik, et al. (1998) *Aust. J. Plant Phys.* 25:335–343). Any possible effect of C1 and B-Peru on isoflavonoid levels was not assayed. Expression of a CRC chimera in an isoflavonoid-producing plant alters the levels of isoflavonoids in the transgenic plant. Soybean plants expressing the CRC chimera contain higher levels of daidzein and lower levels of genistein, with the total daidzein to total genistein ratios being increased, when compared to an untransformed plant (U.S. patent application 60/297981 cofiled with the present on Jun. 13, 2002).

The physiological benefits associated with isoflavonoids in both plants and humans make the manipulation of their contents in crop plants highly desirable. For example, increasing levels of isoflavonoids in soybean seeds increases the efficiency of extraction and lowers the cost of isoflavone-related products sold today for use in either reduction of serum cholesterol or in estrogen replacement therapy. Therefore there is a need to enhance the level of isoflavonoids in isoflavonoid-producing plants. Combining suppression of flavanone 3-hydroxylase (F3H) with activation of the phenylpropanoid pathway is one method to accomplish this goal.

SUMMARY OF THE INVENTION

The invention concerns a method of increasing isoflavonoid production in an isoflavonoid-producing plant, the method comprising:

a) transforming a plant with (1) a first recombinant DNA construct comprising a polynucleotide selected from the group consisting of: (i) a polynucleotide encoding all or part of a flavanone 3-hydroxylase; (ii) a polynucleotide from 5' and/or 3' ends of an isolated nucleic acid fragment which encodes flavanone 3-hydroxylase; or (iii) a polynucleotide comprising (i) and (ii); and (2) at least one second recombinant DNA construct comprising a polynucleotide encoding a C1 myb transcription factor and a R myc-type transcription factor; and b) growing the transformed plant of (a); and c) evaluating the plant or plant part obtained from the transformed plant for an increased quantity of isoflavonoid in the transformed plant or plant part as compared plant or plant parts obtained from an untransformed plant.

In a second embodiment, the first recombinant DNA construct described above comprises a promoter operably linked, in a sense or anti-sense orientation, to a polynucleotide encoding all or part of a flavanone 3-hydroxylase, or a promoter operably linked to a stem-loop structure selected from the group consisting of: (1) a structure wherein the loop comprises the polynucleotide nucleotide encoding all or part of a flavanone 3-hydroxylase and (2) a structure wherein the stem comprises the polynucleotide nucleotide encoding all or part of a flavanone 3-hydroxylase.

In a third embodiment, the isoflavonoid-producing plant is selected from the group consisting of soybean, clover, mung bean, lentil, hairy vetch, alfalfa, lupine, sugar beet, and snow pea. Also of interest are seeds or plant parts of a plant transformed with a recombinant expression construct of the invention from which isoflavonoid-containing products can be obtained or extracted.

In a fourth embodiment, this invention concerns a food or beverage incorporating these isoflavonoid-containing products.

In a fifth embodiment, this invention concerns a method of producing an isoflavonoid-containing product which comprises: (a) cracking the seeds obtained from plants transformed with any of the recombinant expression constructs of the invention to remove the meats from the hulls; and (b) flaking the meats obtained in step (a) to obtain the desired flake thickness.

In a sixth embodiment, the invention concerns an isoflavonoid-producing plant comprising in its genome:

(a) a first recombinant DNA construct comprising a polynucleotide selected from the group consisting of: (i) a polynucleotide encoding all or part of a flavanone 3-hydroxylase; (ii) a polynucleotide from 5' and/or 3' ends of an isolated nucleic acid fragment which encodes flavanone 3-hydroxylase; or (iii) a polynucleotide comprising (i) and (ii); and (b) at least one second recombinant DNA construct comprising a polynucleotide encoding a C1 myb transcription factor and a R myc-type transcription factor; wherein seeds obtained from the transformed plant have an increased quantity of isoflavonoid as compared to seeds obtained from an untransformed plant.

BRIEF DESCRIPTION OF THE DRAWINGS AND SEQUENCE LISTINGS

The invention can be more fully understood from the following detailed description and the accompanying Sequence Listing which form a part of this application.

FIG. 10 depicts the total isoflavones as well as the genistin, daidzin, and glycitin levels observed for individual R2 seeds from transformed plants expressing the F3H construct together with the CRC chimeric construct.

Figure 1:
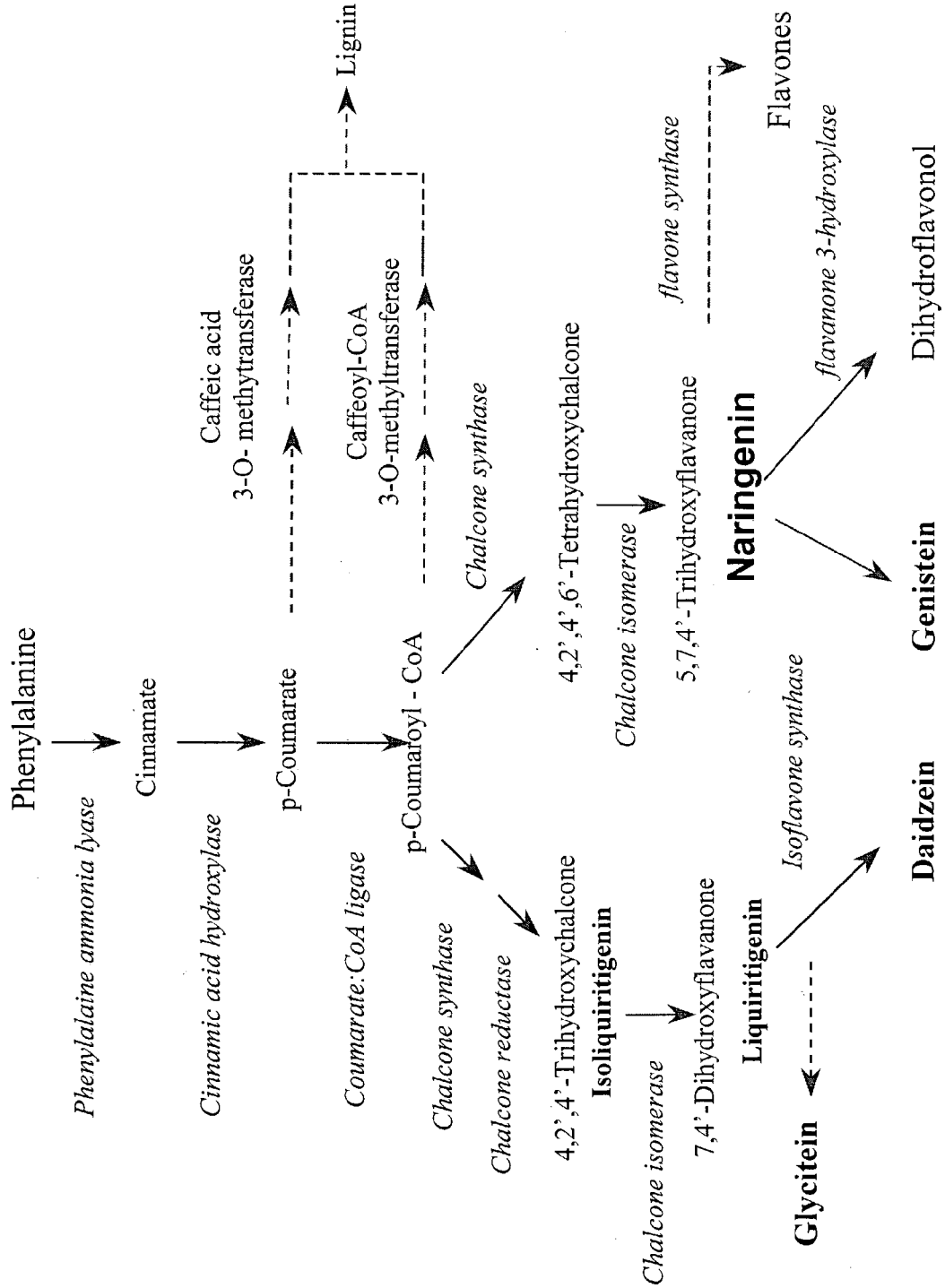
FIG. 1 depicts the soybean biosynthetic pathway from phenylalanine to glycitein, daidzein, genistein, and dihydroflavonol.

The following sequence descriptions and Sequences Listing attached hereto comply with the rules governing nucleotide and/or amino acid sequence disclosures in patent applications as set forth in 37 C.F.R. §1.821–1.825. The Sequence Listing contains the one letter code for nucleotide sequence characters and the three letter codes for amino acids as defined in conformity with the IUPAC-IUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

SEQ ID NO:1 is the nucleotide sequence of plasmid pKS151 used for the expression of a fragment of flavonone 3-hydroxylase.

SEQ ID NO:2 is the nucleotide sequence of primer flavanone 3-hydroxylase NotI sense, used to amplify a flavanone 3-hydroxylase fragment from clone sfl1.pk0040.g11.

SEQ ID NO:3 is the nucleotide sequence of primer flavanone 3-hydroxylase NotI antisense, used to amplify a flavanone 3-hydroxylase fragment from clone sfl1.pk0040.g11.

SEQ ID NO:4 is the nucleotide sequence of the cDNA insert in plasmid sfl1.pk0040.g11, encoding a flavanone 3-hydroxylase.

SEQ ID NO:5 is the nucleotide sequence of primer 3, used to detect the presence of the flavanone 3-hydroxylase construct in tranformed plants.

SEQ ID NO:6 is the nucleotide sequence of primer 4, used to detect the presence of the flavanone 3-hydroxylase construct in tranformed plants.

SEQ ID NO:7 is the nucleotide sequence of primer 5, used to detect the presence of the flavanone 3-hydroxylase construct in tranformed plants.

SEQ ID NO:8 is the nucleotide sequence of primer 6, used to detect the presence of the flavanone 3-hydroxylase construct in tranformed plants.

SEQ ID NO:9 is the nucleotide sequence of primer 1, used to detect the presence of the CRC chimeric construct in tranformed plants.

SEQ ID NO:10 is the nucleotide sequence of primer 2, used to detect the presence of the CRC chimeric construct in tranformed plants.

DETAILED DESCRIPTION OF THE INVENTION

All patents, patent applications and publications cited are incorporated herein by reference in their entirety.

In the context of this disclosure, a number of terms shall be utilized.

The term "isoflavonoid(s)" refers to a large group of polyphenolic compounds, based on a common diphenylpropane skeleton, which occur naturally in plants. This term, as used herein, includes, but is not limited to, the three types of isoflavones in three different forms: the aglycones, daidzein, genistein and glycitein; the glucosides, daidzin, genistin and glycitin; and the malonylglucosides, 6"-O-malonyldaidzin, 6"-O-malonylgenistin and 6"-O-malonylglycitin, as well as, the acetylglucoside forms: 6'-O-acetyldaidzin, 6'-O-acetyl genistin, and 6'-O-acetyl glycitin that are formed during processing.

The term "isoflavonoid-producing plant" refers to a plant in which isoflavonoids naturally occur. Examples of isoflavonoid-producing plants include, but are not limited to, soybean, clover, mung bean, lentil, hairy vetch, alfalfa, lupine, sugar beet, and snow pea. In a more preferred embodiment, the preferred isoflavonoid-producing plant would be soybean. Examples of other isoflavonoid-producing plants can be found in WO 93/23069, published Nov. 25, 1993, the disclosure of which is hereby incorporated by reference.

The term "flavanone 3-hydroxylase" refers to the polypeptide or enzyme that catalyzes the conversion of flavanones to dihydroflavonols.

The term "C1 myb transcription factor" refers to a protein encoded by a *maize* C1 gene and to any protein which is functionally equivalent to a C1 myb transcription factor.

The term "R myc-type transcription factor" refers to a protein with a basic helix-loop-helix domain encoded by a member of the R/B gene family and to any protein that is functionally equivalent to an R myc-type transcription factor.

The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions involves a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions involves the use of higher temperatures in which the washes are identical to those above except for the temperature of the final two 30 min washes in 0.2×SSC, 0.5% SDS was increased to 60° C. Another preferred set of highly stringent conditions involves the use of two final washes in 0.1×SSC, 0.1% SDS at 65° C.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into a genome by a transformation procedure. An "allele" is one of several alternative forms of a gene occupying a given locus on a chromosome. When all the alleles present at a given locus on a chromosome are the same that plant is homozygous at that locus. If the alleles present at a given locus on a chromosome differ that plant is heterozygous at that locus.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters which cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B. (1989) *Biochemistry of Plants* 15:1–82.

Among the most commonly used promoters are the nopaline synthase (NOS) promoter (Ebert et al. (1987) *Proc. Natl. Acad. Sci. U.S.A.* 84:5745–5749), the octapine synthase (OCS) promoter, caulimovirus promoters such as the cauliflower mosaic virus (CaMV) 19S promoter (Lawton et al. (1987) *Plant Mol Biol.* 9:315–324), the CaMV 35S promoter (Odell et al. (1985) *Nature* 313:810–812), and the figwort mosaic virus 35S promoter, the light inducible promoter from the small subunit of rubisco, the Adh promoter (Walker et al. (1987) *Proc. Natl. Acad. Sci. U.S.A.* 84:6624–66280, the sucrose synthase promoter (Yang et al. (1990) *Proc. Natl. Acad. Sci. U.S.A.* 87:4144–4148), the R gene complex promoter (Chandler et al. (1989) *Plant Cell* 1:1175–1183), the chlorophyll a/b binding protein gene promoter, etc. Other commonly used promoters are, the promoters for the potato tuber ADPGPP genes, the sucrose synthase promoter, the granule bound starch synthase promoter, the glutelin gene promoter, the *maize* waxy promoter, Brittle gene promoter, and Shrunken 2 promoter, the acid chitinase gene promoter, and the zein gene promoters (15 kD, 16 kD, 19 kD, 22 kD, and 27 kD; Perdersen et al. (1982) *Cell* 29:1015–1026). A plethora of promoters is described in WO 00/18963, published on Apr. 6, 2000, the disclosure of which is hereby incorporated by reference.

The "translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Mol. Biotech.* 3:225–236).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript. An RNA transcript is referred to as the mature RNA when it is an RNA sequence derived from post-transcriptional processing of the primary transcript.

"Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

The term "expression", as used herein, refers to the production of a functional end-product e.g., a mRNA or a protein (precursor or mature).

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. Preferred methods of cell transformation for rice, corn, and other monocots are the particle-accelerated or "gene gun" transformation technology (Klein et al., (1987) *Nature* (*London*) 327:70–73; U.S. Pat. No. 4,945,050), and an *Agrobacterium*-mediated method using an appropriate Ti plasmid containing the transgene (Ishida Y. et al., 1996, *Nature Biotech.* 14:745–750).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989. Transformation methods are well known to those skilled in the art and are described above.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

The term "recombinant" refers to an artificial combination of two otherwise separated segments of sequence, e.g., by chemical synthesis or by the manipulation of isolated segments of nucleic acids by genetic engineering techniques.

The terms "recombinant construct", "expression construct", "chimeric construct", "construct" and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al. (1998) *Plant J* 16:651–659; and Gura (2000) *Nature* 404:804–808). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication WO 99/53050 published on Oct. 21, 1999). This increases the frequency of co-suppression in the recovered transgenic plants. Another variation describes the use of plant viral sequences to direct the suppression, or "silencing", of proximal mRNA encoding sequences (PCT Publication WO 98/36083 published on Aug. 20, 1998). Both of these co-suppressing phenomena have not been elucidated mechanistically, although recent genetic evidence has begun to unravel this complex situation (Elmayan et al. (1998) *Plant Cell* 10:1747–1757).

The present invention concerns a method of increasing isoflavonoid production in an isoflavonoid-producing plant, said method comprising: a) transforming a plant with (1) a first recombinant DNA construct comprising a polynucleotide selected from the group consisting of: (i) a polynucleotide encoding all or part of a flavanone 3-hydroxylase; (ii) a polynucleotide from 5' and/or 3' ends of an isolated nucleic acid fragment which encodes flavanone 3-hydroxylase; or (iii) a polynucleotide comprising (i) and (ii); and (2) at least one second recombinant DNA construct comprising a polynucleotide encoding a C1 myb transcription factor and a R myc-type transcription factor; and b) growing the transformed plant of (a); and c) valuating the plant or plant parts obtained from the transformed plant for an increased quantity of isoflavonoid in the transformed plant or plant part as compared plant or plant part obtained from an untransformed plant.

The first recombinant DNA construct that may be used to transform plants of the present invention may comprise:

(i) a polynucleotide encoding all or part of a flavanone 3-hydroxylase;

(ii) a polynucleotide from 5' and/or 3' ends of an isolated nucleic acid fragment which encodes flavanone 3-hydroxylase; or (iii) a polynucleotide comprising (i) and (ii).

The polynucleotide mentioned above in (i), (ii), or (iii) may be operably linked to a promoter in a sense orientation or an antisense orientation, or may be forming part of a stem loop structure with the polynucleotide forming either the loop or the stem.

The second recombinant DNA construct, comprising a polynucleotide encoding a C1 myb transcription factor and an R myc-type transcription factor, which can be used to transform an isoflavonoid-producing plant, may comprise:

(a) the polynucleotide encoding a C1 myb transcription factor and the polynucleotide encoding an R myc-type transcription factor can be entirely separate, e.g., one polynucleotide may comprise a promoter operably linked to an isolated nucleic acid fragment encoding a C1 myb transcription factor and another separate polynucleotide may comprise a promoter operably linked to an isolated nucleic acid fragment encoding an R-myc type transcription factor;

(b) the polynucleotide encoding a C1 myb transcription factor and the polynucleotide encoding an R myc-type transcription factor can be in a single construct comprising at least one promoter operably linked to an isolated nucleic acid fragment encoding a C1 myb transcription factor and at least one promoter operably linked to an isolated nucleic acid fragment encoding an R-myc type transcription factor; and (c) the polynucleotide encoding a C1 myb transcription factor and the polynucleotide encoding an R myc-type transcription factor can be in a single construct comprising a promoter operably linked to an isolated nucleic acid fragment encoding all or a part of a C1 myb transcription factor and an isolated nucleic acid fragment encoding all or a part of an R-myc type transcription factor such that a fusion protein combining the two encoded proteins is produced.

The polynucleotide comprising a polynucleotide encoding at least a portion of a flavanone 3-hydroxylase and the polynucleotide comprising a C1 myb transcription factor and an R-myc type factor may each form part of at least one recombinant DNA construct, or may form part of one single recombinant DNA expression construct.

The transformed plant is then grown under conditions suitable for the expression of the recombinant DNA construct or constructs. Expression of the recombinant DNA construct or constructs alters the quantity of isoflavonoid of the transformed plant compared to the quantity of isoflavonoid of an untransformed plant.

In a more preferred, embodiment, an isoflavonoid-producing plant can be transformed with a recombinant expression construct comprising a promoter operably linked to a flavanone 3-hydroxylase and a recombinant expression construct comprising a promoter operably linked to an isolated nucleic acid fragment encoding a chimeric transcription factor comprising the *maize* R coding region situated between the C1 DNA binding domain and the C1 activation domain.

The regeneration, development and cultivation of plants from single plant protoplast transformants or from various transformed explants is well known in the art (Weissbach and Weissbach, In.: Methods for Plant Molecular Biology, (Eds.), Academic Press, Inc., San Diego, Calif. (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue.

The particular method of regeneration will depend on the starting plant tissue and the particular plant species to be regenerated.

Methods for transforming dicots, primarily by use of *Agrobacterium tumefaciens*, and obtaining transgenic plants have been published for cotton (U.S. Pat. Nos. 5,004,863, 5,159,135, 5,518,908); soybean (U.S. Pat. No. 5,569,834, U.S. Pat. No. 5,416,011, McCabe et. al., *BiolTechnology* 6:923 (1988), Christou et al., *Plant Physiol.* 87:671–674 (1988)); *Brassica* (U.S. Pat. No. 5,463,174); peanut (Cheng et al., *Plant Cell Rep.* 15:653–657 (1996), McKently et al., *Plant Cell Rep.* 14:699–703 (1995)); papaya; and pea (Grant et al., *Plant Cell Rep.* 15:254–258, (1995)).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454–457 (1988); Marcotte et al., *Plant Cell* 1:523–532 (1989); McCarty et al., *Cell* 66:895–905 (1991); Hattori et al., *Genes Dev.* 6:609–618 (1992); Goff et al., *EMBO J.* 9:2517–2522 (1990)).

Transient expression systems may be used to functionally dissect gene constructs (see generally, Maliga et al., Methods in Plant Molecular Biology, Cold Spring Harbor Press (1995)). It is understood that any of the nucleic acid molecules of the present invention can be introduced into a plant cell in a permanent or transient manner in combination with other genetic elements such as vectors, promoters, enhancers etc.

In addition to the above discussed procedures, practitioners are familiar with the standard resource materials which describe, specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, New York (1997)).

Any promoter can be used in accordance with the method of the invention. Thus, the origin of the promoter chosen to drive expression of the coding sequence is not critical as long as it has sufficient transcriptional activity to accomplish the invention by expressing translatable mRNA for the desired nucleic acid fragments in the desired host tissue. The promoter for use in the present invention may be selected from the group consisting of a seed-specific promoter, root-specific promoter, vacuole-specific promoter, and an embryo-specific promoter.

Examples of a seed-specific promoter include, but are not limited to, the promoter for β-conglycinin (Chen et al. (1989) *Dev. Genet.* 10:112–122), the napin promoter, and the phaseolin promoter. Other tissue-specific promoters that may be used to accomplish the invention include, but are not limited to, the chloroplast glutamine synthase (GS2) promoter (Edwards et al. (1990) *Proc. Natl. Acad. Sci. U.S.A.* 87:3459–3463), the chloroplast fructose-1,6-biophosphatase promoter (Lloyd et al. (1991) *Mol. Gen. Genet.* 225:209–2216), the nuclear photosynthetic (ST-LS1) promoter (Stockhaus et al. (1989) *EMBO J.* 8:2445–2451), the serine/threonine kinase (PAL) promoter, the glucoamylase promoter, the promoters for the Cab genes (cab6, cab-1, and cab-1R, Yamamoto et al. (1994) *Plant Cell Physiol.* 35:773–778; Fejes et al. (1990) *Plant Mol. Biol.* 15:921–932; Lubberstedt et al. (1994) *Plant Physiol.* 104: 997–1006; Luan et al. (1992) *Plant Cell* 4:971–981), the pyruvate orthophosphate dikanase promoter (Matsuoka et al. (1993) *Proc. Natl. Acad. Sci. U.S.A.* 90:9586–9590), the LhcB promoter (Cerdan et al. (1997) *Plant Mol. Biol.* 33:245–255), the PsbP promoter (Kretsch et al. (1995) *Plant Mol. Biol.* 28:219–229), the SUC2 sucrose H+ symporter promoter (Truernit et al. (1995) Planta 196:564–570), and the promoters for the thylakoid membrane genes (psaD, psaF, psaE, PC, FNR, atpC, atpD), etc.

Also within the scope of this invention are seeds or plant parts obtained from such transformed plants. Plant parts include differentiated and undifferentiated tissues, including but not limited to, roots, stems, shoots, leaves, pollen, seeds, tumor tissue, and various forms of cells and culture such as single cells, protoplasts, embryos, and callus tissue. The plant tissue may be in plant or in organ, tissue or cell culture.

In another aspect, this invention concerns an isoflavonoid-containing product high in total isoflavonoids obtained from the seeds or plant parts obtained from the transformed plants described herein. Examples of such an isoflavonoid-containing product include, but are not limited to, protein isolate, protein concentrate, meal, grits, full fat and defatted flours, textured proteins, textured flours, textured concentrates and textured isolates. In still another aspect, this invention concerns an isoflavonoid-containing product high in isoflavonoids extracted from the seeds or plant parts obtained from the transformed plants described herein. An extracted product could then used in the production of pills, tablets, capsules or other similar dosage forms made to contain a high concentration of isoflavonoids.

Methods for obtaining such products are well known to those skilled in the art. For example, in the case of soybean, such products can be obtained in a variety of ways. Conditions typically used to prepare soy protein isolates have been described by [Cho, et al, (1981) U.S. Pat. No. 4,278,597; Goodnight, et al. (1978) U.S. Pat. No. 4,072,670]. Soy protein concentrates are produced by three basic processes: acid leaching (at about pH 4.5), extraction with alcohol (about 55–80%), and denaturing the protein with moist heat prior to extraction with water. Conditions typically used to prepare soy protein concentrates have been described by Pass [(1975) U.S. Pat. No. 3,897,574] and Campbell et al. [(1985) in New Protein Foods, ed. by Altschul and Wilcke, Academic Press, Vol. 5, Chapter 10, *Seed Storage Proteins*, pp 302–338].

"Isoflavonoid-containing protein products" can be defined as those items produced from seed of a suitable plant which are used in feeds, foods and/or beverages. For example, "soy protein products" can include, but are not limited to, those items listed in Table 1. "Soy protein products".

TABLE 1

Soy Protein Products Derived from Soybean Seeds[a]

| Whole Soybean Products | Processed Soy Protein Products |
|---|---|
| Roasted Soybeans | Full Fat and Defatted Flours |
| Baked Soybeans | Soy Grits |
| Soy Sprouts | Soy Hypocotyls |
| Soy Milk | Soybean Meal |
|  | Soy Milk |
| Specialty Soy Foods/Ingredients | Soy Protein Isolates |
| Soy Milk | Soy Protein Concentrates |
| Tofu | Textured Soy Proteins |
| Tempeh | Textured Flours and Concentrates |
| Miso | Textured Concentrates |
| Soy Sauce | Textured Isolates |
| Hydrolyzed Vegetable Protein | |
| Whipping Protein | |

[a]See Soy Protein Products: Characteristics, Nutritional Aspects and Utilization (1987). Soy Protein Council.

"Processing" refers to any physical and chemical methods used to obtain the products listed in Table 1 and includes, but is not limited to, heat conditioning, flaking and grinding, extrusion, solvent extraction, or aqueous soaking and extraction of whole or partial seeds. Furthermore, "processing" includes the methods used to concentrate and isolate soy protein from whole or partial seeds, as well as the various traditional Oriental methods in preparing fermented soy food products. Trading Standards and Specifications have been established for many of these products (see National Oilseed Processors Association Yearbook and Trading Rules 1991–1992). Products referred to as being "high protein" or "low protein" are those as described by these Standard Specifications. "NSI" refers to the Nitrogen Solubility Index as defined by the American Oil Chemists' Society Method Ac4 41. "KOH Nitrogen Solubility" is an indicator of soybean meal quality and refers to the amount of nitrogen soluble in 0.036 M KOH under the conditions as described by Araba and Dale [(1990) *Poult. Sci.* 69:76–83]. "White" flakes refer to flaked, dehulled cotyledons that have been defatted and treated with controlled moist heat to have an NSI of about 85 to 90. This term can also refer to a flour with a similar NSI that has been ground to pass through a No. 100 U.S. Standard Screen size. "Cooked" refers to a soy protein product, typically a flour, with an NSI of about 20 to 60. "Toasted" refers to a soy protein product, typically a flour, with an NSI below 20. "Grits" refer to defatted, dehulled cotyledons having a U.S. Standard screen size of between No. 10 and 80. "Soy Protein Concentrates" refer to those products produced from dehulled, defatted soybeans by three basic processes: acid leaching (at about pH 4.5), extraction with alcohol (about 55–80%), and denaturing the protein with moist heat prior to extraction with water. Conditions typically used to prepare soy protein concentrates have been described by Pass [(1975) U.S. Pat. No. 3,897,574; Campbell et al., (1985) in New Protein Foods, ed. by Altschul and Wilcke, Academic Press, Vol. 5, Chapter 10, *Seed Storage Proteins*, pp 302–338]. "Extrusion" refers to processes whereby material (grits, flour or concentrate) is passed through a jacketed auger using high pressures and temperatures as a means of altering the texture of the material. "Texturing" and "structuring" refer to extrusion processes used to modify the physical characteristics of the material. The characteristics of these processes, including thermoplastic extrusion, have been described previously [Atkinson (1970) U.S. Pat. No. 3,488,770, Horan (1985) In *New Protein Foods*, ed. by Altschul and Wilcke, Academic Press, Vol. 1A, Chapter 8, pp 367–414]. Moreover, conditions used during extrusion processing of complex foodstuff mixtures that include soy protein products have been described previously [Rokey (1983) *Feed Manufacturing Technology III*, 222–237; McCulloch, U.S. Pat. No. 4,454,804].

Also, within the scope of this invention are food, food supplements, food bars, and beverages which have incorporated therein an isoflavonoid-containing product of the invention. The beverage can be in a liquid or in a dry powdered form.

The foods to which the isoflavonoid-containing product of the invention can be incorporated/added include almost all foods/beverages. For example, there can be mentioned meats such as ground meats, emulsified meats, marinated meats, and meats injected with an isoflavonoid-containing product of the invention; beverages such as nutritional beverages, sports beverages, protein fortified beverages, juices, milk, milk alternatives, and weight loss beverages; cheeses such as hard and soft cheeses, cream cheese, and cottage cheese; frozen desserts such as ice cream, ice milk, low fat frozen desserts, and non-dairy frozen desserts; yogurts; soups; puddings; bakery products; and salad dressings; and dips and spreads such as mayonnaise and chip dips. The isoflavonoid-containing product can be added in an amount selected to deliver a desired dose to the consumer of the food and/or beverage.

In still another aspect this invention concerns a method of producing an isoflavonoid-containing product which comprises: (a) cracking the seeds obtained from transformed plants of the invention to remove the meats from the hulls; and (b) flaking the meats obtained in step (a) to obtain the desired flake thickness.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Construction of Plasmids for Transformation of Glycine Max

The ability to increase the levels of isoflavonoids in transgenic plants was tested. For this purpose, expression cassettes were prepared that would be capable of suppressing flavanone 3-hydroxylase, or that would express the CRC chimera. Plasmids AC21 and pOY135 were prepared and the methods used to prepare them are described below.

Preparation of Plasmid AC21

Figure 2:
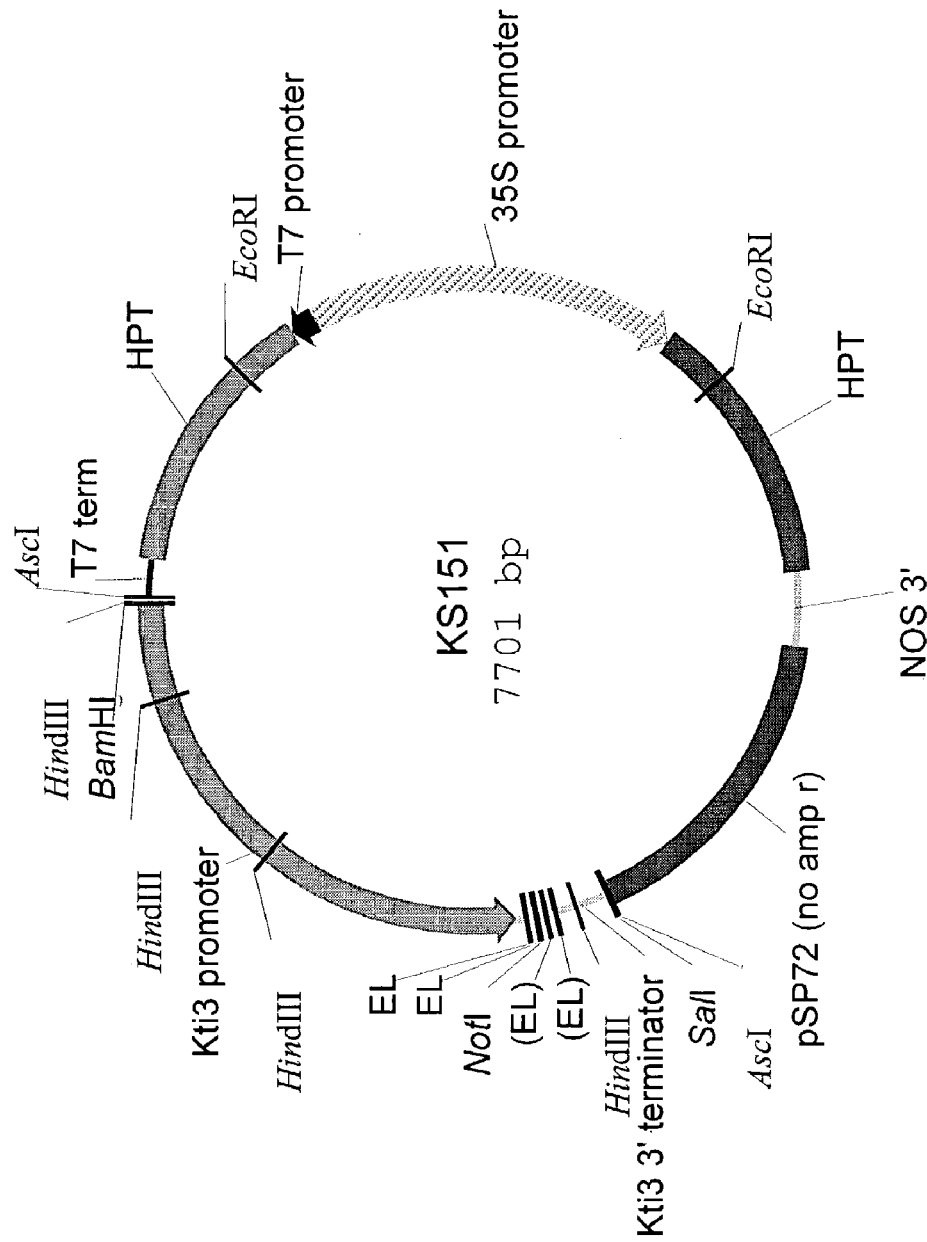
FIG. 2 depicts a representation of the seed-specific expression vector pKS151. The two copies of the 36-nucleotide sequence are indicated by "EL", and the inverted repeat of the 36-nucleotide sequence are indicated by "(EL)".

Plasmid AC21 was prepared to test the effect of the expression of a soybean flavanone 3-hydroxylase on the soybean isoflavonoid profile. To prepare plasmid AC21, expression cassettes were prepared containing a seed-specific expression promoter followed by nucleotide sequences that promote formation of a stem loop structure surrounding sequences encoding a portion of a soybean flavanone 3-hydroxylase gene, and followed by a transcription termination signal. It is well understood by those skilled in the art that other sequences commonly used in molecular manipulations may be used here. These sequences may include any seed-specific promoter, any structure that promotes stem-loop formation, any portion of the gene or genes of interest inserted in sense or anti-sense orientation with respect to the promoter and stem-loop structure, and any termination signal. It is also well known by those skilled in the art that sequences promoting stem-loop formation are not always required for gene suppression. Preparation of plasmid AC21 follows:

Plasmid AC21 was prepared by inserting a polynucleotide encoding a portion of a soybean flavanone 3-hydroxylase in the seed-specific expression vector pKS151. Vector pKS151 is depicted in FIG. 2 and its nucleotide sequence is shown in SEQ ID NO:1. This vector has been described in PCT Publication WO 02/00904, published 3 Jan. 2002, and is derived from the commercially available vector pSP72 (Promega, Madison, Wis.).

To produce pKS151 vector pSP72 was modified by:

a) deleting nucleotide sequences 1135 through 1995 corresponding to the beta lactamase coding region;

b) inserting sequences encoding HPT under the control of the T7 promoter and termination signals, for expression of the HPT enzyme in bacteria;

c) adding a cassette comprising the 35S promoter/HPT/NOS 3' for constitutive expression of the HPT enzyme in plants; and d) adding a cassette comprising a unique Not 1 restriction endonuclease site surrounded by sequences that promote formation of a stem structure which are flanked by the KTi promoter and KTi 3' terminator sequences.

Expression of HPT by two different promoters allows the selection for growth in the presence of hygromycin in bacterial and plant systems. The promoter and transcription terminator from the gene encoding the kunitz trypsin inhibitor 3 (KTi3; Jofuku, K. D. and Goldberg, R. B. (1989) *Plant Cell* 1:1079–1093) in the cassette include about 2088 nucleotides upstream (5') from the translation initiation codon and about 202 nucleotides downstream (3') from the translation stop codon of KTi 3. Between the 5' and 3' regions is a unique Not I restriction endonuclease site. The Not I site is flanked by nucleotide sequences that promote formation of a "stem-loop" structure when nucleotide sequences of the gene of interest are inserted at the Not I site. This "stem-loop" structure will have the sequences of the gene of interest forming the loop. The stem structure is formed by two copies of a 36 nucleotide sequence at the 5' end of the Not I site and an inverted repeat of the same two 36-nucleotide sequences at the 3' end.

To create plasmid AC21 sequences encoding a portion of a soybean flavanone 3-hydroxylase gene were inserted in the Not I site of pKS151. The flavanone 3-hydroxylase sequences were obtained by PCR amplification using clone sfl1.pk0040.g11 as template and primers flavanone 3-hydroxylase-Not1-sense (shown in SEQ ID NO:2) and flavanone 3-hydroxylase-Not1-antisense (shown in SEQ ID NO:3). Clone sfl1.pk0040.g11 was originally identified as encoding a flavanone 3-hydroxylase in PCT publication WO 99/43825, published 2 Sep. 1999. The nucleotide sequence of the cDNA insert in clone sfl1. pk0040.g11 is shown in SEQ ID NO:4.

(SEQ ID NO:2)
5'-GCG GCC GCA TGG CAC CAA CAG CCA AG-3'

(SEQ ID NO:3)
5"-GCG GCC GCA TCC GTG TGG CGC TTC AG-3'

The amplification reaction was performed using advantage 2 polymerase and GC melt reagent (1 mM final concentration) and following to the manufacturer's (Clontech, Palo Alto, Calif.) protocol. The resulting amplified DNA fragment was first cloned into TopoTA vector (Invitrogen, Carlsbad, Calif.). The fragment was liberated from the TopoTA vector by Not I digestion and was purified from an agarose gel using Qiagen Gel Purification Kit (Qiagen, Valencia, Calif.). The purified DNA fragment was inserted into the Not I site of vector pKS151 to produce the plasmid AC21.

Preparation of Plasmid pOY135

Plasmid pOY135 contains, flanked by Hind IIII restriction endonuclease sites, a CRC chimeric construct inserted between the phaseolin promoter and polyadenylation signal sequences. The CRC chimeric construct contains, between Sma I sites and in the 5' to 3' orientation, *maize* nucleotide sequences encoding a) the C1 myb domain to amino acid 125;

b) the entire coding region of the Lc allele of R (amino acids 1 through 160); and c) the C1 transcription activation domain (from amino acid 126 to the C-terminus of C1).

The CRC chimeric construct was isolated from plasmid pDP7951 (described in PCT Publication WO 00/44909, published Aug. 3, 2000, and bearing ATCC deposit No. PTA371) and inserted into vector pCW 108N. Vector pCW108N is derived from the commercially-available vector pUC 18 (Gibco-BRL) and contains between Hind III sites:

a) a DNA fragment of the phaseolin gene promoter extending from −410 to +77 relative to the transcription start site (Slightom et al. (1991) *Plant Mol. Biol. Man.* B16:1); and b) a 1175 bp DNA fragment including the polyadenylation signal sequence region of the same phaseolin gene (see sequence descriptions in Doyle et al. (1986) *J. Biol. Chem.* 261:9228–9238 and Slightom et al. (1983) *Proc. Natl. Acad. Sci. USA* 80:1897–1901).

Plasmid pCW108N was digested with Asp 718, which cuts between the phaseolin promoter and polyadenylation signal sequence, and the protruding ends filled-in by incubation with T4 DNA polymerase in the presence of dATP, dCTP, dGTP, and dTTP. The DNA fragment containing the CRC chimeric construct was isolated from pDP7951 by digestion with Sma I, purified by agarose.gel electrophoresis, and inserted into the blunt-ended pCW108N to create plasmid pOY135.

Example 2

Transformation of Somatic Soybean Embryo Cultures and Regeneration of Soybean Plants The ability to increase the isoflavonoid levels in transgenic soybean plants was tested by co-transforming soybean somatic embryo cultures with plasmids AC21 and pOY135 or with plasmid AC21 alone, selecting transformants that grew in the presence of hygromycin, allowing plants to regenerate, and measuring the levels of isoflavone produced in seeds.

Soybean embryogenic suspension cultures were transformed with plasmid AC21 in conjunction with plasmid pOY135 by the method of particle gun bombardment.

The following stock solutions and media were used for transformation and regeneration of soybean plants (per Liter):

MS Sulfate 100× stock: 37.0 g $MgSO_4.7H_2O$, 1.69 g $MnSO_4.H_2O$, 0.86 g $ZnSO_4.7H_2O$, 0.0025 g $CuSO_4.5H_2O$.

MS Halides 100× stock: 44.0 g $CaCl_2.2H_2O$, 0.083 g KI, 0.00125 g $CoCl_2.6H_2O$, 17.0 g $KH_2PO_4$, 0.62 g $H_3BO_3$, 0.025 g $Na_2MoO_4.2H_2O$, 3.724 g $Na_2EDTA$, 2.784 g $FeSO_4.7H_2O$.

B5 Vitamin stock: 100.0 g myo-inositol, 1.0 g nicotinic acid, 1.0 g pyridoxine HCl, 10.0 g thiamine.

2,4-D stock: 10 mg/mL

SB55: 10 mL of each MS stock, 1 mL of B5 Vitamin stock, 0.8 g $NH_4NO_3$, 3.033 g $KNO_3$, 1 mL 2,4-D stock, 0.667 g asparagine, pH 5.7.

SB103: 1 pk. Murashige & Skoog salt mixture (Gibco, Carlsbad, Calif.), 60 g maltose, 2 g gelrite, pH 5.7.

SB71-1: B5 salts, 1 ml B5 vitamin stock, 30 g sucrose, 750 mg MgCl2, 2 g gelrite, pH 5.7.

Soybean (of the Jack variety) embryogenic suspension cultures were maintained in 35 mL SB55 liquid media on a rotary shaker (150 rpm) at 28° C. with a mix of fluorescent and incandescent lights providing a 16 hour day, 8 hour night cycle. Cultures were subcultured every 2 to 3 weeks by inoculating approximately 35 mg of tissue into 35 mL of fresh liquid media.

Soybean embryonic suspension cultures were transformed by the method of particle gun bombardment (see Klein et al. (1987) *Nature* 327:70–73) using a DuPont Biolistic PDS1000/He instrument. Embryos were either bombarded with plasmid pAC21 or co-bombarded with plasmid AC21 and plasmid pOY135 in a 1:10 molar ratio. Transformed lines were selected on hygromycin containing medium, and the presence of plasmid pAC21 or the CRC chimeric construct was determined by PCR. Transgenic plants were generated from lines positive for the desired recombinant DNA fragments.

For bombardment, 5 μL plasmid DNA (either 1 μg/μL of pAC21 or a mixture of 0.5 μg/μL pOY135 and 1 μg/μL pAC21), 50 μL 2.5 M CaCl$_2$, and 20 μL 0.1 M spermidine were added to 50 μL of a 60 mg/mL 0.6 μm gold particle suspension. The particle preparation was agitated for 3 minutes, spun in a microfuge for 10 seconds and the supernatant removed. The DNA-coated gold particles were then washed once with 400 μL of 100% ethanol, resuspended in 40 μL of anhydrous ethanol, and sonicated three times for 1 second each. Five μL of the DNA-coated gold particles was then loaded on each macro carrier disk.

Approximately 300 to 400 mg of two-week-old suspension culture was placed in an empty 60 mm×15 mm petri dish and the residual liquid removed from the tissue using a pipette. The tissue was placed about 3.5 inches away from the retaining screen and bombarded twice. Membrane rupture pressure was set at 1100 psi and the chamber was evacuated to −28 inches of Hg. Two plates were bombarded for each experiment and, following bombardment, the tissue was divided in half, placed back into liquid media, and cultured as described above.

Eleven days after bombardment, the liquid media was exchanged with fresh SB55 media containing 50 mg/mL hygromycin. The selective media was refreshed weekly. Seven weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Thus, each new line was treated as an independent transformation event. Soybean suspension cultures can be maintained as suspensions of embryos clustered in an immature developmental stage through subculture or can be regenerated into whole plants by maturation and germination of individual somatic embryos.

Transformed embryogenic clusters were removed from liquid culture and placed on SB103 solid agar media containing no hormones or antibiotics. Embryos were cultured for eight weeks at 26° C. with mixed fluorescent and incandescent lights on a 16 hour day, 8 hour night schedule. During this period, individual embryos were removed from the clusters and analyzed at various stages of embryo development. Lines selected for hygromycin resistance were assayed by PCR for the presence of the CRC chimeric construct and/or the F3H construct contained in plasmid pAC21. The presence of the F3H construct was assayed by amplifying plant tissue using Primer 3 (shown in SEQ ID NO:5) and Primer 4 (shown in SEQ ID NO:6), or using Primer 5 (shown in SEQ ID NO:7) and Primer 6 (shown in SEQ ID NO:8) and separating the amplified product by agarose gel electrophoresis. The presence of the F3H construct was confirmed by the appearance of a 763 base pair fragment when using Primer 3 and Primer 4, or a 656 base pair fragment when using Primer 5 and Primer 6. The presence of the CRC chimeric construct was determined by amplifying plant tissue using Primer 1 (shown in SEQ ID NO:9) and Primer 2 (shown in SEQ ID NO:10) which, when separated by agarose gel electrophoresis, produce a fragment not present in soybean plant tissue not having the CRC chimeric construct.

```
                                            (SEQ ID NO:5)
primer 3:   5'-TCC TCA GTC ACC GAT CTC CAC CC-3'

(SEQ ID NO:6)
primer 4:   5'-CGG ATA TAA TGA GCC GTA AAC A-3'

(SEQ ID NO:7)
primer 5:   5'-TGG ATG GAC GCA GAA GAG AGA TTT G-3'

(SEQ ID NO:8)
primer 6:   5'-CCG ATT CTC CCA ACA TTG CTT ATT C-3'

(SEQ ID NO:9)
primer 1    5'-AGG CGG AAG AAG TGC TGG AAG G-3'

(SEQ ID NO:10)
primer 2    5'-AGG TCC ATT TCG TCG CAG AGG C-3'
```

Somatic embryos became suitable for germination after eight weeks and were then removed from the maturation medium and dried in empty petri dishes for 1 to 5 days. The dried embryos were then planted in SB71-1 medium where they were allowed to germinate under the same lighting and germination conditions described above. Germinated embryos were transferred to sterile soil and grown to maturity. Seeds were harvested.

Example 3

Analysis of Isoflavone Levels in Seeds of Transformants Containing the F3H Construct or the F3H Construct and the CRC Chimeric Construct The quantity of isoflavones in seeds from transgenic plants comprising the F3H construct or comprising the CRC chimeric construct and the F3H construct was assayed. Seeds were ground, the combined powder was extracted with methanol, hydrolyzed with base, and analyzed. Base hydrolysis removes the malonyl group from malonylglucoside conjugates and the three glucoside conjugates (genistin, daidzin, and glycitin) are measured. While aglycones are not measured by this method the amount of aglycones present is in such low quantities as to not affect the final results. Thus the isoflavone numbers are reported as parts per million (ppm) of glucoside conjugates in soybean. A more detailed explanation of the preparation of seed extracts and measurement of isoflavone follows.

Five to eight seeds per transformant were combined and the seeds were ground to a fine powder using a single seed grinder set to the finest setting. One gram of ground soybean seeds was extracted with 40 mL MeOH:water (80:20 v/v) in a 125-mL Erlenmeyer flask at 65° C. on an orbital shaker. After shaking for 2 hours the flask was removed from the shaker and allowed to cool to room temperature. Three mL of 2N NaOH were then added and the flask was returned to an orbital shaker at room temperature for 10 min. The flask was then removed from the shaker and 1-mL glacial acetic acid was added. The sample was diluted to 50 mL with MeOH:water (80:20 v/v) and filtered through 5 μm filter paper in a funnel into another 125-mL Erlenmeyer flask. A mixture of 2.5 mL of sample and 2.5 mL of MeOH:water (80:20 v/v) were diluted with water to 10 mL in a volumetric flask. Particulate material was removed from a sample of 1–1.5 mL by spinning in a microfuge tube, the liquid transferred to a labeled autosampler vial, and analyzed by HPLC using the gradient indicated on Table 2 below.

TABLE 2

HPLC Gradient Settings

| Time (min) | Flow (mL/min) | 1% acetic acid in water (mL) | 1% acetic acid in acetonitrile (mL) |
|---|---|---|---|
| Initial | 1.0 | 90 | 10 |
| 5.0 | 1.0 | 90 | 10 |
| 11.0 | 1.0 | 78 | 22 |
| 12.0 | 2.0 | 0 | 100 |
| 14.5 | 2.0 | 0 | 100 |
| 14.6 | 2.0 | 90 | 10 |
| 16.5 | 1.0 | 90 | 10 |

The HPLC was set to continue acquiring data to 17 minutes. Degas mode was set to continuous, column temperature was set to 30° C., and sample temperature was set to 4° C. The ultraviolet detector was set as follows: sampling rate=10, wavelength=262 nm, autozero=0.1 minutes. The amounts of isoflavones present were determined by comparing the results to a 5-point standard curve conducted using commercially available daidzin, glycitin, and genistin.

Analysis of R1 Seed From Transformation Events with plasmid AC21

Figure 3:
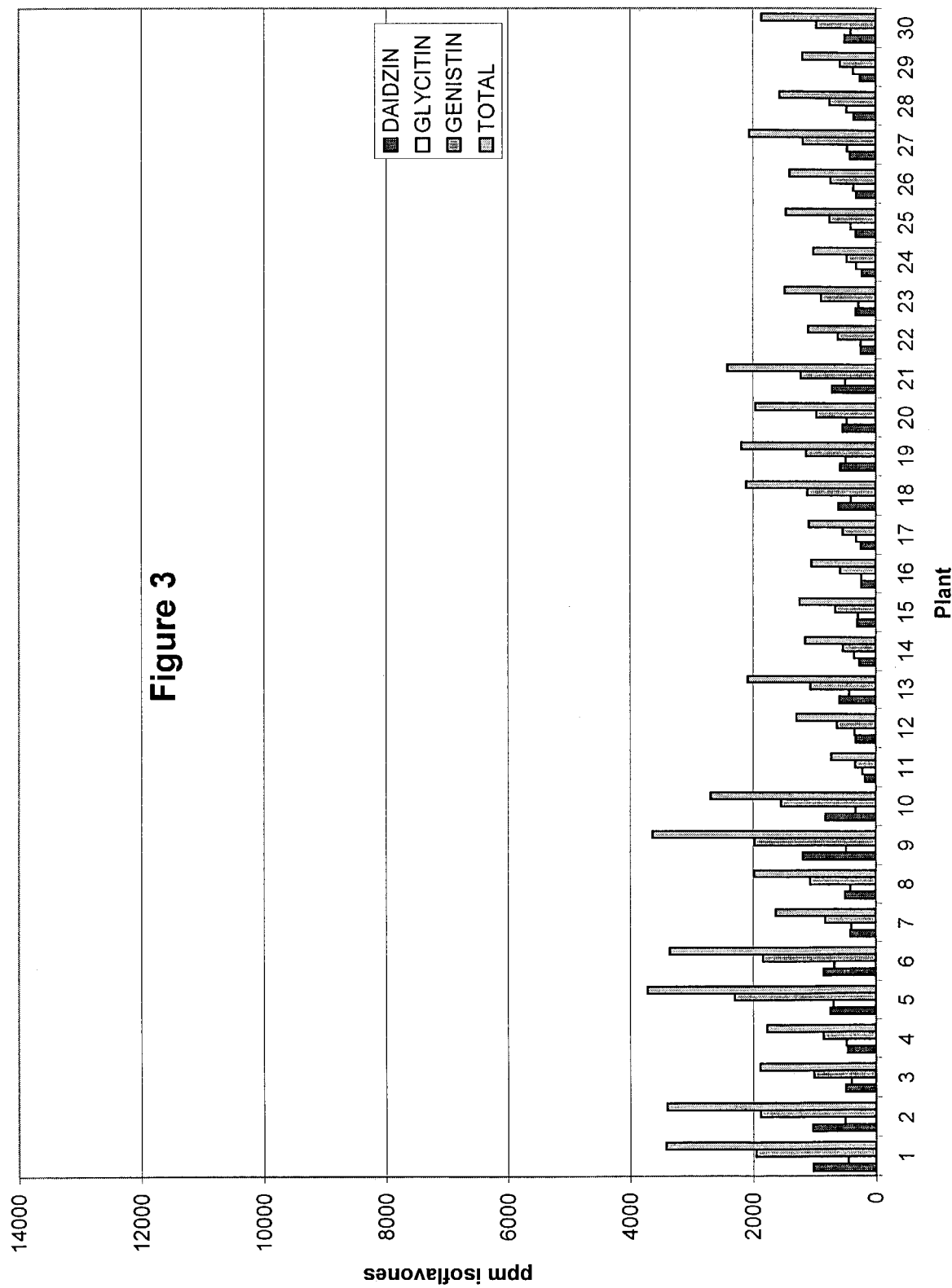
FIG. 3 depicts the total isoflavones as well as the genistin, daidzin, and glycitin levels observed for individual R1 seeds from transformed plants expressing the F3H construct.
Figure 4:
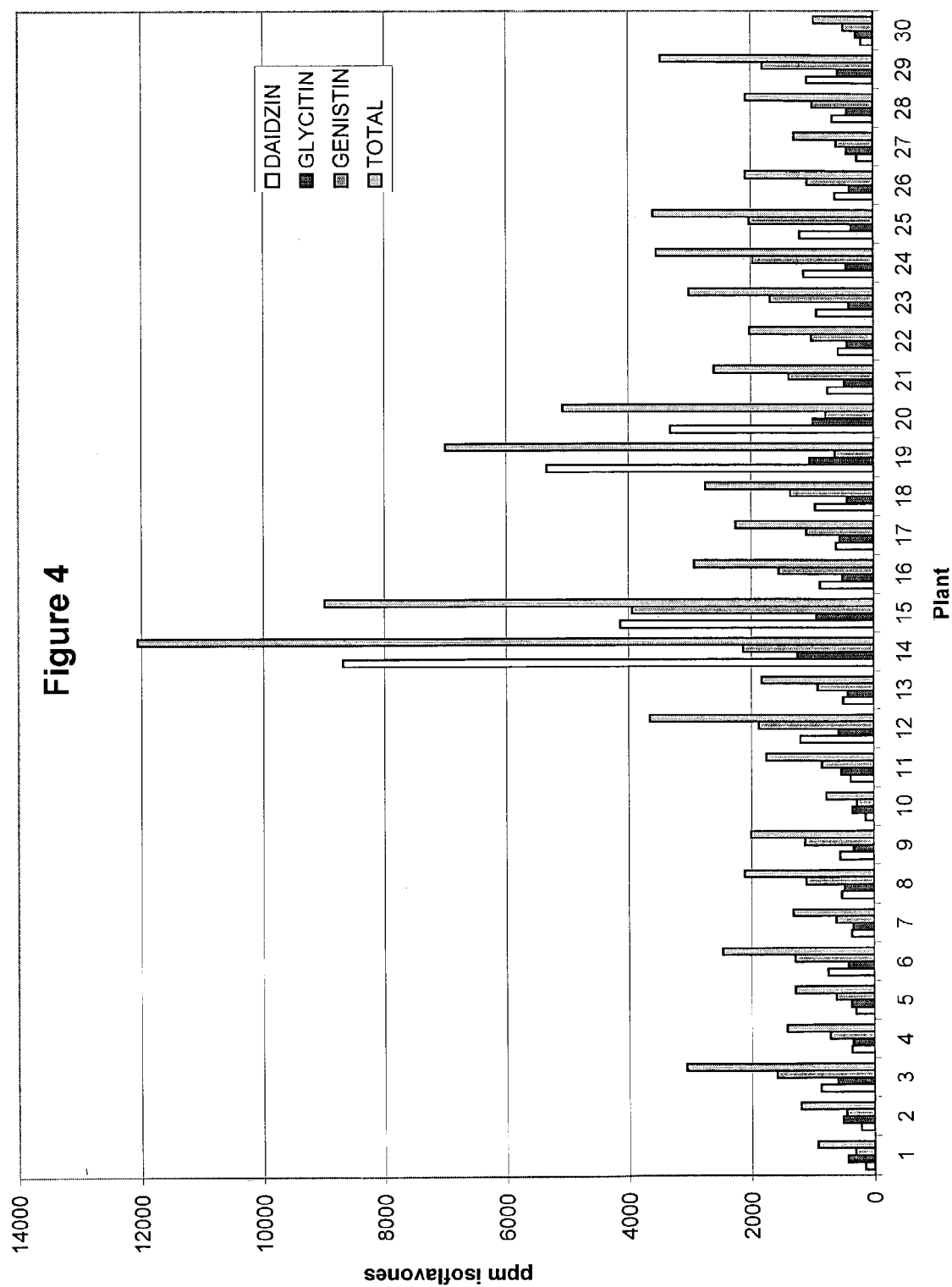
FIG. 4 through FIG. 9 depict the total isoflavones as well as the genistin, daidzin, and glycitin levels observed for individual R1 seeds from transformed plants expressing the F3H construct together with the CRC chimeric construct.
Figure 5:
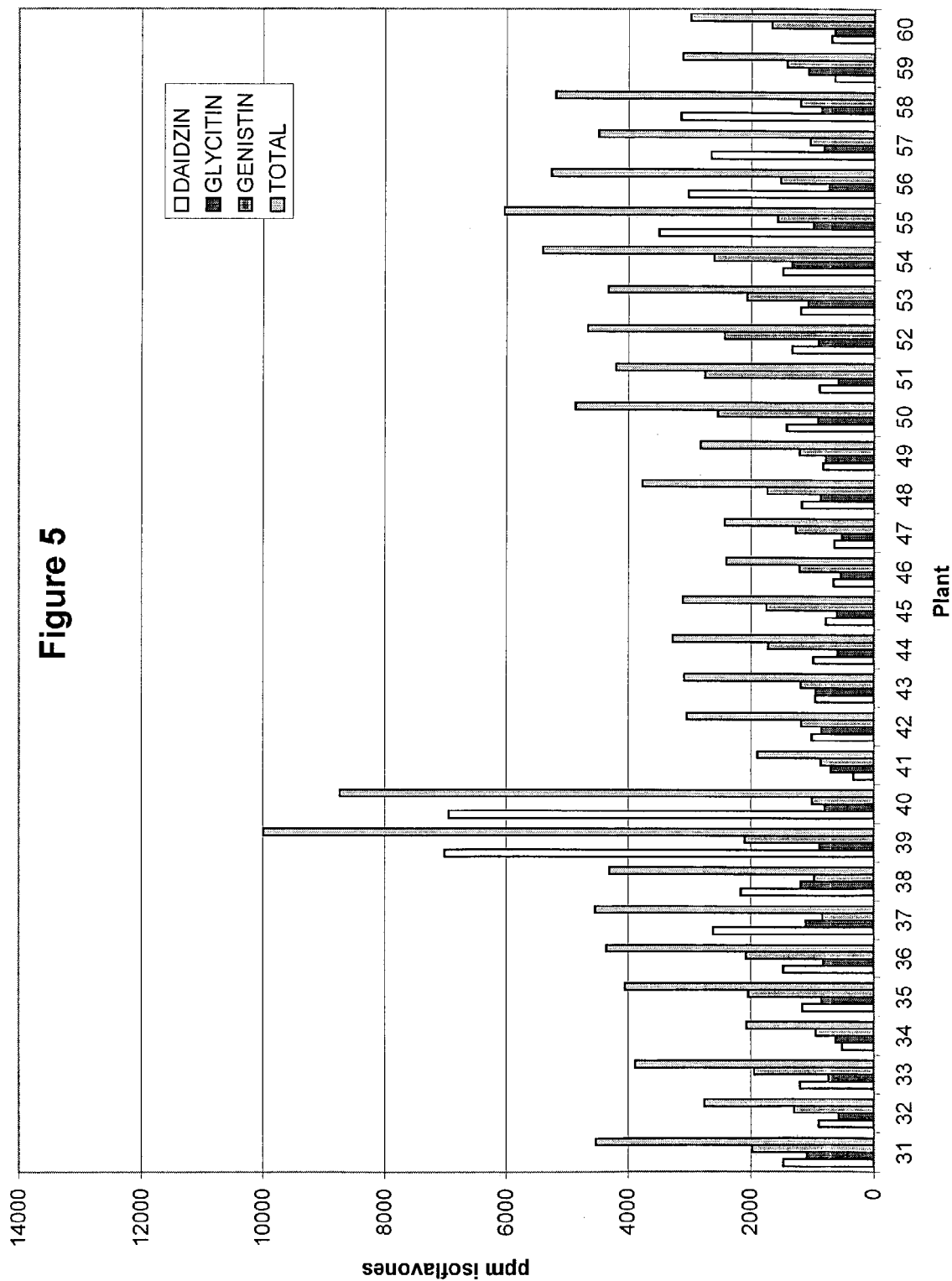
Figure 6:
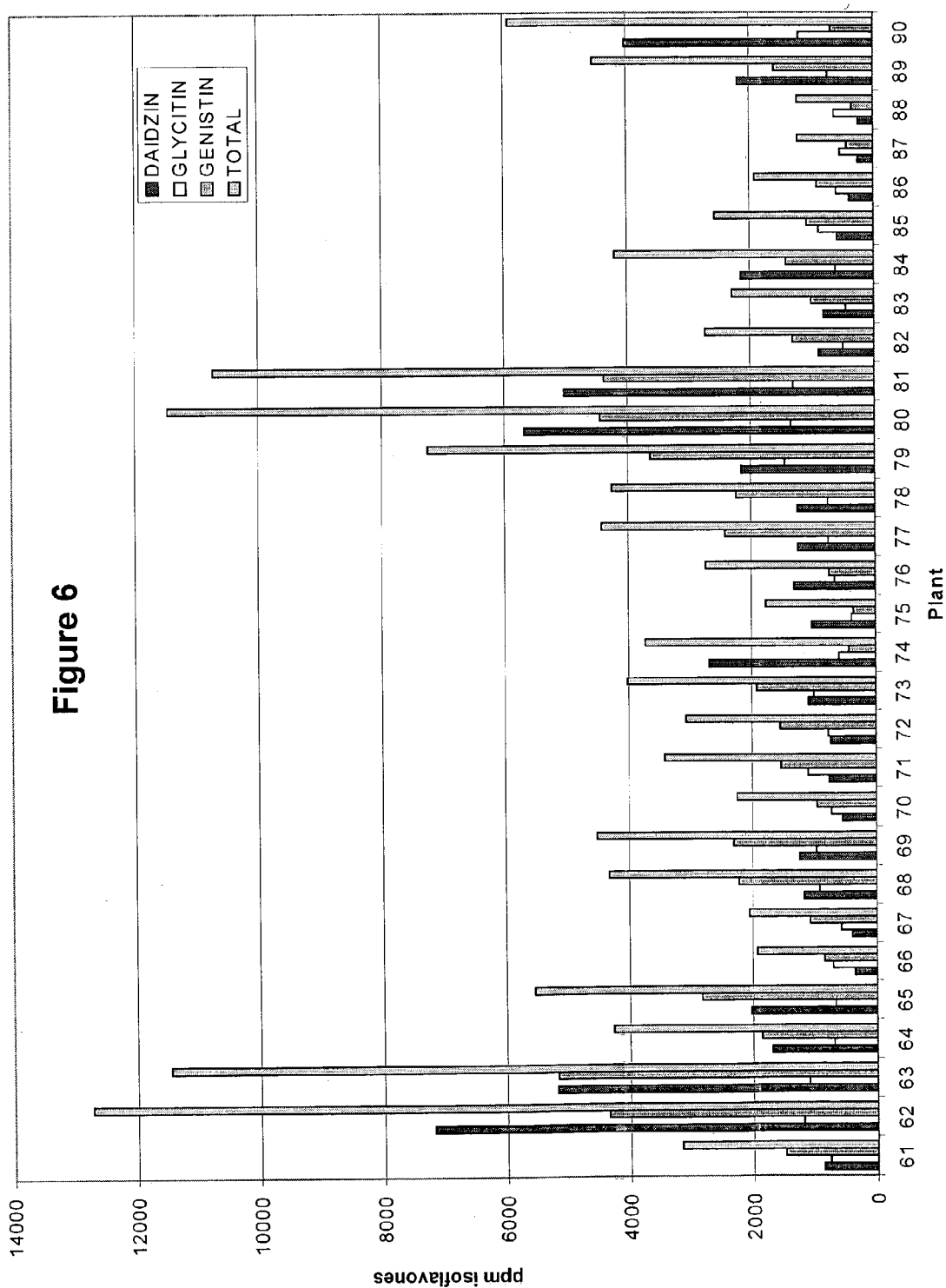
Figure 7:
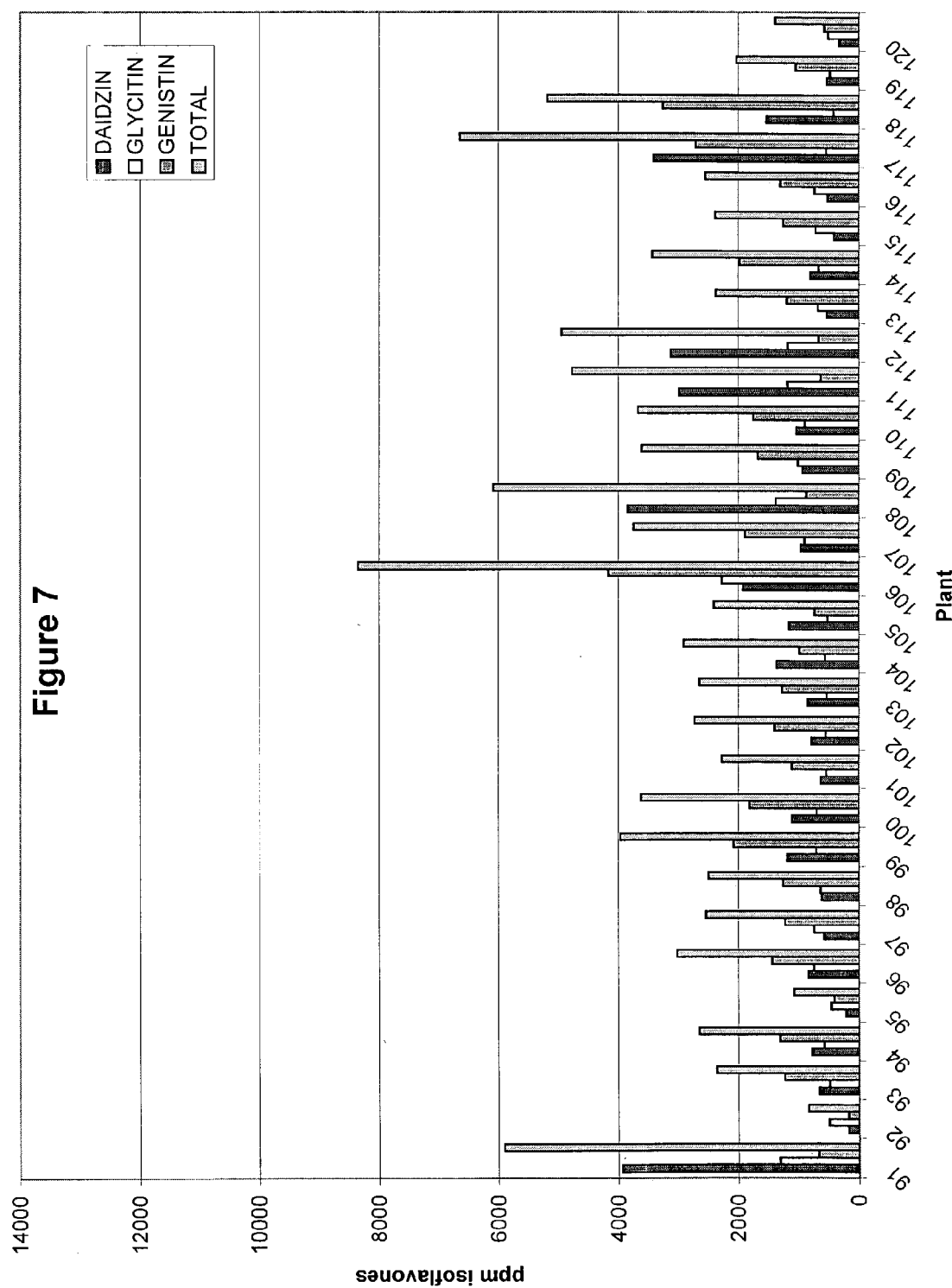
Figure 8:
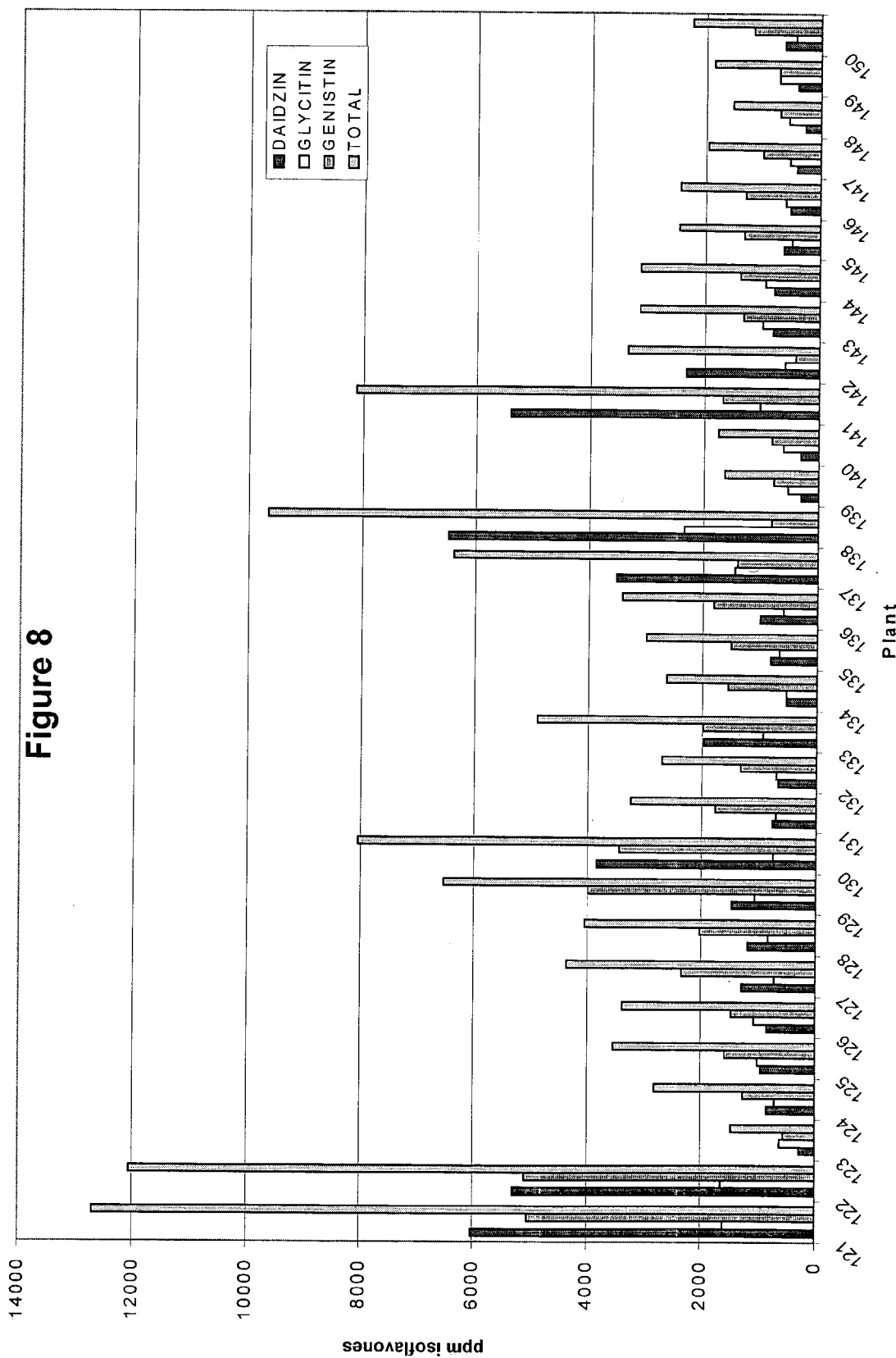
Figure 9:
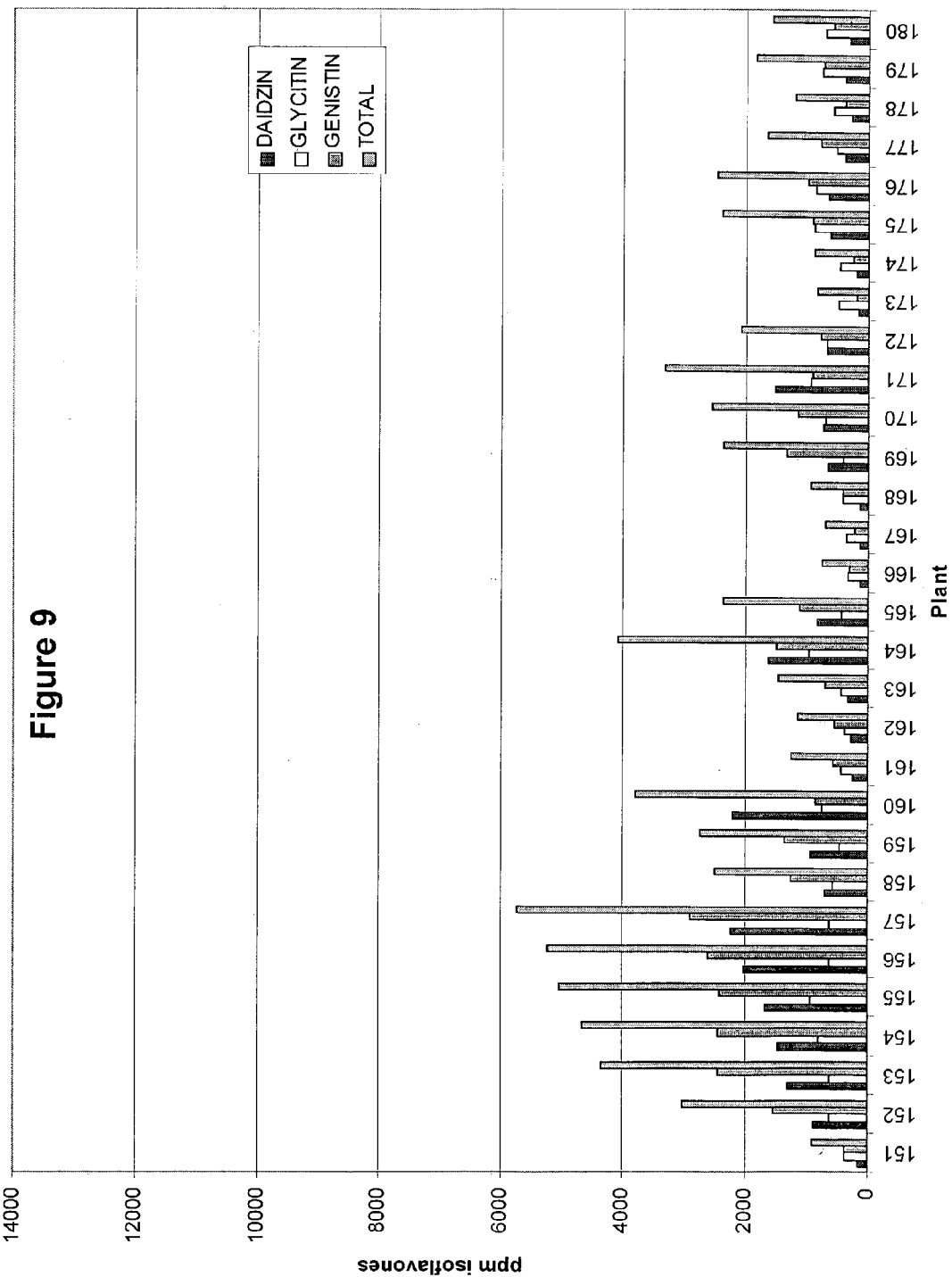

The levels of isoflavones in 27 independent transformation events containing plasmid AC21 alone were assayed. Table 3 and FIG. 3 present the level of isoflavones (total), as well as the isoflavone components (daidzin, glycitin, or genistin), of samples of transgenic seeds positive for the F3H construct. For ease of understanding, the plants from which the seeds are derived are numbered 1 through 30 in the figure, and the plant number indicated in the table.

TABLE 3

Isoflavone and Isoflavone Component Levels in R1 Seed Transgenic for Plasmid AC21

| Plant | Plant No. | Daidzin | Glycitin | Genistin | Total |
|---|---|---|---|---|---|
| 1 | 264-2-4-1 | 1019 | 448 | 1957 | 3424 |
| 2 | 264-2-4-2 | 1026 | 496 | 1885 | 3407 |
| 3 | 264-2-5-1 | 490 | 391 | 1007 | 1888 |
| 4 | 264-2-5-3 | 455 | 472 | 846 | 1774 |
| 5 | 264-2-6-1 | 737 | 685 | 2298 | 3720 |
| 6 | 264-2-6-2 | 845 | 673 | 1842 | 3360 |
| 7 | 264-3-3-1 | 412 | 397 | 820 | 1629 |
| 8 | 264-3-3-2 | 500 | 414 | 1070 | 1984 |
| 9 | 290-1-6-1 | 1183 | 480 | 1975 | 3638 |
| 10 | 290-1-6-3 | 812 | 327 | 1542 | 2681 |
| 11 | 290-2-14-2 | 173 | 215 | 331 | 719 |
| 12 | 290-2-23-1 | 323 | 341 | 629 | 1293 |
| 13 | 290-2-23-2 | 587 | 432 | 1061 | 2080 |
| 14 | 290-2-23-3 | 263 | 348 | 533 | 1144 |
| 15 | 290-2-24-1 | 300 | 285 | 654 | 1239 |
| 16 | 290-2-24-3 | 231 | 235 | 575 | 1041 |
| 17 | 262-1-4-1 | 237 | 315 | 532 | 1084 |
| 18 | 262-1-4-2 | 601 | 399 | 1109 | 2109 |
| 19 | 262-1-4-3 | 574 | 482 | 1131 | 2187 |
| 20 | 262-1-10-1 | 531 | 470 | 962 | 1963 |
| 21 | 262-1-10-3 | 701 | 490 | 1218 | 2409 |
| 22 | 262-2-1-1 | 237 | 243 | 615 | 1095 |
| 23 | 262-2-1-2 | 318 | 276 | 884 | 1478 |
| 24 | 262-2-7-1 | 223 | 317 | 470 | 1010 |
| 25 | 262-2-7-2 | 319 | 398 | 745 | 1462 |
| 26 | 262-2-7-3 | 317 | 356 | 727 | 1400 |
| 27 | 262-3-6-1 | 415 | 460 | 1184 | 2059 |
| 28 | 262-3-6-2 | 351 | 469 | 745 | 1565 |
| 29 | 262-3-8-1 | 253 | 363 | 577 | 1193 |
| 30 | 262-3-8-2 | 502 | 399 | 963 | 1864 |

The levels of isoflavone accumulation did not vary significantly in any of the transformants positive only for plasmid AC21 (F3H construct) when compared to wild type (untransformed) soybeans of the Jack variety.

Analysis of R1 Seed from Transformation Events with Plasmids AC21 and pOY135

The levels of isoflavones in plants from independent transformation events containing plasmid AC21 and plasmid pOY135 were assayed. Table 4 and FIG. 4 through FIG. 9 present the level of isoflavones, as well as the isoflavone components, of samples of transgenic seeds positive for the F3H construct and the CRC chimeric construct. For ease of understanding, the plants from which the seeds are derived are numbered 1 through 180 in the figures, and the plant number indicated in the table.

TABLE 4

Isoflavone and Isoflavone Component Levels in R1 Seed Transgenic for Plasmids AC21 and pOY135

| Plant | Plant No. | Daidzin | Glycitin | Genistin | Total |
|---|---|---|---|---|---|
| 1 | 275-2-2-1 | 157 | 446 | 320 | 923 |
| 2 | 275-2-2-2 | 227 | 517 | 466 | 1211 |
| 3 | 275-2-3-2 | 870 | 595 | 1598 | 3063 |
| 4 | 276-2-4-1 | 366 | 348 | 717 | 1431 |
| 5 | 276-2-4-2 | 304 | 370 | 618 | 1292 |
| 6 | 276-4-6-2 | 746 | 430 | 1293 | 2469 |
| 7 | 276-4-6-3 | 362 | 340 | 617 | 1319 |
| 8 | 277-4-3-1 | 522 | 480 | 1112 | 2114 |
| 9 | 277-4-3-2 | 549 | 334 | 1128 | 2011 |
| 10 | 277-4-4-1 | 138 | 351 | 281 | 770 |
| 11 | 277-4-4-2 | 382 | 530 | 842 | 1755 |
| 12 | 277-4-6-2 | 1203 | 576 | 1876 | 3655 |
| 13 | 277-4-6-3 | 498 | 426 | 907 | 1831 |
| 14 | 277-6-3-1 | 8684 | 1246 | 2130 | 12060 |
| 15 | 277-6-3-2 | 4126 | 919 | 3936 | 8981 |
| 16 | 277-6-7-1 | 867 | 506 | 1549 | 2923 |
| 17 | 277-6-7-3 | 611 | 546 | 1097 | 2254 |
| 18 | 277-7-6-1 | 940 | 434 | 1364 | 2738 |
| 19 | 279-2-1-1 | 5326 | 1049 | 627 | 7002 |
| 20 | 279-2-1-2 | 3308 | 988 | 770 | 5066 |
| 21 | 279-3-3-2 | 740 | 473 | 1384 | 2597 |
| 22 | 279-3-3-3 | 570 | 436 | 1013 | 2019 |
| 23 | 281-2-3-1 | 914 | 405 | 1683 | 3003 |
| 24 | 281-2-3-2 | 1136 | 445 | 1962 | 3543 |
| 25 | 281-2-3-3 | 1205 | 364 | 2024 | 3593 |
| 26 | 281-2-3-4 | 619 | 387 | 1083 | 2088 |
| 27 | 281-2-3-5 | 263 | 434 | 594 | 1291 |
| 28 | 281-2-3-6 | 658 | 426 | 997 | 2082 |
| 29 | 282-3-1-1 | 1083 | 576 | 1811 | 3469 |
| 30 | 282-3-3-2 | 202 | 279 | 485 | 967 |
| 31 | 3090-1-1-2 | 1463 | 1093 | 1976 | 4532 |
| 32 | 3090-1-1-3 | 896 | 560 | 1290 | 2746 |
| 33 | 3090-1-2-2 | 1200 | 733 | 1948 | 3882 |
| 34 | 3090-1-2-3 | 509 | 618 | 943 | 2070 |
| 35 | 3090-1-3-1 | 1162 | 849 | 2039 | 4051 |
| 36 | 3090-1-3-2 | 1464 | 815 | 2076 | 4354 |
| 37 | 3090-1-6-1 | 2603 | 1104 | 835 | 4541 |
| 38 | 3090-1-6-2 | 2156 | 1184 | 966 | 4305 |
| 39 | 3090-1-8-1 | 7018 | 878 | 2094 | 9990 |
| 40 | 3090-1-8-2 | 6950 | 789 | 1001 | 8739 |
| 41 | 3090-1-9-1 | 326 | 699 | 862 | 1888 |
| 42 | 3090-1-9-2 | 1007 | 851 | 1178 | 3036 |
| 43 | 3090-1-9-3 | 953 | 942 | 1187 | 3083 |
| 44 | 3090-1-10-1 | 980 | 582 | 1707 | 3269 |
| 45 | 3090-1-10-2 | 776 | 591 | 1741 | 3108 |
| 46 | 3090-1-12-2 | 656 | 533 | 1208 | 2397 |
| 47 | 3090-1-12-3 | 640 | 515 | 1270 | 2425 |
| 48 | 3090-1-15-1 | 1173 | 865 | 1726 | 3765 |
| 49 | 3090-1-15-2 | 821 | 779 | 1208 | 2808 |
| 50 | 3090-1-17-1 | 1417 | 909 | 2535 | 4861 |
| 51 | 3090-1-17-2 | 890 | 568 | 2743 | 4200 |
| 52 | 3090-1-18-1 | 1335 | 905 | 2428 | 4668 |
| 53 | 3090-1-18-2 | 1190 | 1075 | 2064 | 4329 |
| 54 | 3090-1-18-3 | 1476 | 1333 | 2592 | 5401 |
| 55 | 3090-2-2-1 | 3499 | 980 | 1564 | 6043 |
| 56 | 3090-2-2-2 | 3018 | 725 | 1515 | 5259 |
| 57 | 3090-2-3-1 | 2644 | 808 | 1038 | 4491 |

TABLE 4-continued

Isoflavone and Isoflavone Component Levels
in R1 Seed Transgenic for Plasmids AC21 and pOY135

| Plant | Plant No. | Daidzin | Glycitin | Genistin | Total |
|---|---|---|---|---|---|
| 58 | 3090-2-3-2 | 3139 | 853 | 1196 | 5189 |
| 59 | 3090-2-4-1 | 635 | 1063 | 1415 | 3113 |
| 60 | 3090-2-4-2 | 690 | 637 | 1658 | 2985 |
| 61 | 3090-2-4-3 | 879 | 778 | 1502 | 3160 |
| 62 | 3090-2-5-1 | 7185 | 1202 | 4342 | 12729 |
| 63 | 3090-2-5-2 | 5184 | 1105 | 5170 | 11459 |
| 64 | 3090-2-6-1 | 1698 | 699 | 1864 | 4261 |
| 65 | 3090-2-6-3 | 2037 | 675 | 2831 | 5543 |
| 66 | 3090-2-7-1 | 359 | 715 | 857 | 1932 |
| 67 | 3090-2-7-2 | 397 | 582 | 1081 | 2060 |
| 68 | 3090-2-8-1 | 1173 | 929 | 2228 | 4330 |
| 69 | 3090-2-8-2 | 1245 | 973 | 2306 | 4523 |
| 70 | 3090-2-9-1 | 555 | 734 | 962 | 2251 |
| 71 | 3090-2-9-2 | 765 | 1106 | 1543 | 3414 |
| 72 | 3090-2-11-1 | 739 | 781 | 1553 | 3073 |
| 73 | 3090-2-11-2 | 1092 | 1006 | 1919 | 4017 |
| 74 | 3090-2-12-1 | 2689 | 591 | 438 | 3719 |
| 75 | 3090-2-12-2 | 1027 | 391 | 356 | 1774 |
| 76 | 3090-2-14-2 | 1324 | 660 | 752 | 2736 |
| 77 | 3090-2-15-1 | 1252 | 761 | 2420 | 4433 |
| 78 | 3090-2-15-2 | 1255 | 769 | 2239 | 4263 |
| 79 | 3090-2-15-3 | 2158 | 1462 | 3628 | 7248 |
| 80 | 3090-2-16-1 | 5673 | 1357 | 4444 | 11474 |
| 81 | 3090-2-16-2 | 5025 | 1318 | 4388 | 10730 |
| 82 | 3090-4-1-1 | 899 | 507 | 1322 | 2727 |
| 83 | 3090-4-1-3 | 816 | 452 | 1018 | 2286 |
| 84 | 3090-4-3-2 | 2147 | 620 | 1427 | 4194 |
| 85 | 3090-4-4-1 | 587 | 894 | 1085 | 2566 |
| 86 | 3090-4-4-2 | 394 | 601 | 920 | 1915 |
| 87 | 3090-4-6-1 | 254 | 542 | 430 | 1226 |
| 88 | 3090-4-6-2 | 245 | 637 | 350 | 1233 |
| 89 | 3090-4-7-1 | 2195 | 747 | 1603 | 4545 |
| 90 | 3090-4-8-1 | 4024 | 1207 | 684 | 5915 |
| 91 | 3090-4-8-2 | 3931 | 1317 | 660 | 5908 |
| 92 | 3090-4-10-1 | 171 | 486 | 179 | 836 |
| 93 | 3090-4-11-1 | 646 | 482 | 1232 | 2359 |
| 94 | 3090-4-11-3 | 772 | 569 | 1312 | 2654 |
| 95 | 3090-4-12-1 | 214 | 456 | 404 | 1074 |
| 96 | 3090-4-12-3 | 838 | 746 | 1437 | 3021 |
| 97 | 3090-4-13-1 | 576 | 741 | 1221 | 2538 |
| 98 | 3090-4-13-2 | 608 | 625 | 1262 | 2495 |
| 99 | 3090-4-16-1 | 1182 | 704 | 2080 | 3966 |
| 100 | 3090-4-16-2 | 1112 | 693 | 1812 | 3618 |
| 101 | 3090-4-18-1 | 618 | 532 | 1115 | 2266 |
| 102 | 3090-5-1-1 | 783 | 540 | 1404 | 2728 |
| 103 | 3090-5-1-2 | 849 | 526 | 1273 | 2648 |
| 104 | 3090-5-4-1 | 1370 | 553 | 989 | 2912 |
| 105 | 3090-5-4-2 | 1156 | 511 | 735 | 2402 |
| 106 | 3090-6-1-2 | 1920 | 2267 | 4167 | 8354 |
| 107 | 3090-6-1-3 | 962 | 900 | 1884 | 3746 |
| 108 | 3090-6-2-1 | 3840 | 1379 | 871 | 6091 |
| 109 | 3090-6-2-2 | 929 | 1009 | 1670 | 3609 |
| 110 | 3090-6-2-3 | 1032 | 895 | 1743 | 3670 |
| 111 | 3090-6-3-1 | 2977 | 1180 | 620 | 4776 |
| 112 | 3090-6-3-2 | 3119 | 1177 | 658 | 4953 |
| 113 | 3090-6-6-1 | 512 | 668 | 1186 | 2366 |
| 114 | 3090-6-6-2 | 799 | 655 | 1974 | 3428 |
| 115 | 3090-6-7-1 | 412 | 711 | 1252 | 2375 |
| 116 | 3090-6-7-2 | 511 | 736 | 1300 | 2546 |
| 117 | 3090-6-8-1 | 3405 | 533 | 2703 | 6642 |
| 118 | 3090-6-8-2 | 1529 | 415 | 3249 | 5193 |
| 119 | 3090-6-9-1 | 516 | 469 | 1045 | 2029 |
| 120 | 3090-6-9-3 | 325 | 502 | 566 | 1393 |
| 121 | 3090-7-2-1 | 6031 | 1617 | 5053 | 12701 |
| 122 | 3090-7-2-3 | 5301 | 1654 | 5102 | 12057 |
| 123 | 3090-7-3-1 | 293 | 621 | 560 | 1475 |
| 124 | 3090-7-3-2 | 843 | 710 | 1265 | 2818 |
| 125 | 3090-7-4-1 | 955 | 1006 | 1588 | 3549 |
| 126 | 3090-7-4-3 | 844 | 1072 | 1471 | 3387 |
| 127 | 3090-7-5-1 | 1295 | 729 | 2342 | 4366 |
| 128 | 3090-7-5-2 | 1190 | 831 | 2029 | 4050 |
| 129 | 3090-7-6-1 | 1475 | 1068 | 3994 | 6536 |
| 130 | 3090-7-6-2 | 3845 | 752 | 3449 | 8047 |
| 131 | 3090-7-7-1 | 765 | 712 | 1771 | 3247 |
| 132 | 3090-7-7-2 | 669 | 706 | 1330 | 2706 |
| 133 | 3090-7-8-1 | 1979 | 937 | 1985 | 4902 |
| 134 | 3090-7-10-2 | 536 | 540 | 1555 | 2631 |
| 135 | 3090-7-11-1 | 818 | 663 | 1507 | 2987 |
| 136 | 3090-7-11-2 | 996 | 601 | 1820 | 3416 |
| 137 | 3090-7-12-1 | 3528 | 1448 | 1405 | 6381 |
| 138 | 3090-7-12-2 | 6486 | 2346 | 814 | 9647 |
| 139 | 3090-7-14-1 | 318 | 539 | 784 | 1642 |
| 140 | 3090-7-14-2 | 321 | 619 | 822 | 1761 |
| 141 | 3090-8-1-1 | 5399 | 1030 | 1689 | 8118 |
| 142 | 3090-8-1-3 | 2332 | 602 | 422 | 3357 |
| 143 | 3090-8-5-1 | 815 | 995 | 1335 | 3145 |
| 144 | 3090-8-5-2 | 798 | 949 | 1389 | 3137 |
| 145 | 3090-8-8-2 | 635 | 500 | 1326 | 2462 |
| 146 | 3090-8-8-3 | 527 | 607 | 1307 | 2442 |
| 147 | 3090-8-10-1 | 423 | 540 | 1005 | 1968 |
| 148 | 3090-8-10-2 | 263 | 562 | 713 | 1538 |
| 149 | 3090-8-11-1 | 419 | 725 | 728 | 1871 |
| 150 | 3090-8-11-2 | 634 | 449 | 1169 | 2252 |
| 151 | 3090-8-13-1 | 154 | 374 | 364 | 892 |
| 152 | 3090-8-13-2 | 875 | 618 | 1528 | 3021 |
| 153 | 3090-8-14-1 | 1288 | 618 | 2433 | 4340 |
| 154 | 3090-8-14-2 | 1457 | 790 | 2429 | 4675 |
| 155 | 3090-8-14-3 | 1679 | 939 | 2421 | 5039 |
| 156 | 3090-8-15-2 | 2011 | 597 | 2610 | 5219 |
| 157 | 3090-8-15-3 | 2234 | 608 | 2891 | 5733 |
| 158 | 3092-1-4-1 | 684 | 564 | 1248 | 2496 |
| 159 | 3092-2-3-1 | 936 | 440 | 1343 | 2718 |
| 160 | 3092-2-3-2 | 2210 | 744 | 843 | 3797 |
| 161 | 3092-2-7-1 | 243 | 437 | 563 | 1243 |
| 162 | 3092-2-7-2 | 260 | 367 | 523 | 1150 |
| 163 | 3092-3-2-2 | 324 | 421 | 702 | 1446 |
| 164 | 3092-3-9-1 | 1622 | 958 | 1491 | 4072 |
| 165 | 3092-3-9-2 | 809 | 424 | 1116 | 2350 |
| 166 | 3092-3-21-1 | 134 | 318 | 294 | 746 |
| 167 | 3092-3-21-2 | 142 | 345 | 201 | 687 |
| 168 | 3092-3-21-3 | 144 | 403 | 389 | 935 |
| 169 | 3092-3-24-1 | 635 | 407 | 1327 | 2369 |
| 170 | 3092-3-24-2 | 723 | 696 | 1127 | 2546 |
| 171 | 3092-4-10-1 | 1504 | 929 | 893 | 3326 |
| 172 | 3092-4-10-2 | 651 | 658 | 768 | 2077 |
| 173 | 3092-5-1-1 | 162 | 472 | 185 | 819 |
| 174 | 3092-5-1-3 | 196 | 463 | 227 | 885 |
| 175 | 3092-5-8-1 | 615 | 881 | 893 | 2389 |
| 176 | 3092-5-8-2 | 630 | 852 | 989 | 2470 |
| 177 | 3092-8-3-1 | 359 | 501 | 776 | 1635 |
| 178 | 3092-8-3-2 | 257 | 549 | 381 | 1188 |
| 179 | 3092-8-6-1 | 383 | 740 | 705 | 1828 |
| 180 | 3092-8-6-2 | 302 | 701 | 559 | 1561 |

Analyses of these transgenic events indicated that 16 out of 180 plants containing both the CRC chimeric construct and the F3H construct showed isoflavone levels greater than 7000 ppm with the highest level being 12729 ppm. These plants accumulate isoflavones to levels significantly higher than wild type while retaining the wild type profile of the individual isoflavone components. For example seed 277-6-3-1 showed 12060 ppm isoflavones and seed 279-2-1-1 showed 7002 ppm isoflavones while wild type (untransformed) soybeans of the Jack variety show an average of 3000 ppm isoflavones.

Analysis of R2 Seeds

The isoflavone levels of R2 seeds derived from plants containing plasmid AC21 and plasmid pOY135 were determined. Table 5 and FIG. 10 present the level of isoflavones, as well as the isoflavone components, of samples of R2 transgenic seeds derived from seeds positive for the F3H construct and the CRC chimeric construct. In the genotype column, a plus sign (+) means that the progeny is PCR positive for both CRC and F3H constructs while a minus (−) means that the progeny is PCR negative for both CRC and F3H constructs, *ND is indicated where the genotype was not determined. PCR amplification was carried out as described in Example 2. Thus the high isoflavonoid phenotype is inherited in the R2 generation. For ease of understanding, the plants from which the seeds are derived are numbered 1 through 39 in the figures, and the plant number indicated in the table.

TABLE 5

Isoflavone and Isoflavone Component Levels in R2 Seed Derived from Transgenic plants comprising Plasmids AC21 and pOY135

| Plant | R1 Plant No. | R2 No. | Genotype | Daidzin | Glycitin | Genistin | Total |
|---|---|---|---|---|---|---|---|
| 1 | 279-2-1-1 | 835-1 | − | 242 | 445 | 494 | 1181 |
| 2 | 279-2-1-1 | 835-2 | − | 152 | 198 | 330 | 680 |
| 3 | 279-2-1-1 | 835-3 | + | 2395 | 1182 | 2712 | 6289 |
| 4 | 279-2-1-1 | 836-1 | − | 229 | 316 | 464 | 1008 |
| 5 | 279-2-1-1 | 836-2 | + | 743 | 470 | 542 | 1756 |
| 6 | 279-2-1-1 | 836-3 | + | 750 | 752 | 1503 | 3004 |
| 7 | 279-2-1-1 | 837-1 | + | 1390 | 693 | 1762 | 3845 |
| 8 | 279-2-1-1 | 837-2 | − | 143 | 231 | 281 | 654 |
| 9 | 279-2-1-1 | 838-1 | − | 348 | 449 | 669 | 1466 |
| 10 | 279-2-1-1 | 838-2 | + | 2561 | 1086 | 1201 | 4848 |
| 11 | 279-2-1-2 | 839-1 | + | 1499 | 777 | 612 | 2887 |
| 12 | 279-2-1-2 | 839-2 | + | 987 | 631 | 322 | 1940 |
| 13 | 279-2-1-2 | 839-3 | + | 1638 | 698 | 604 | 2940 |
| 14 | 279-2-1-2 | 840-1 | − | 292 | 362 | 589 | 1243 |
| 15 | 279-2-1-2 | 840-2 | − | 364 | 335 | 754 | 1452 |
| 16 | 279-2-1-2 | 841-1 | − | 153 | 234 | 359 | 746 |
| 17 | 279-2-1-2 | 842-1 | − | 319 | 330 | 671 | 1319 |
| 18 | 279-2-1-2 | 842-2 | + | 2209 | 921 | 542 | 3672 |
| 19 | 277-6-3-1 | 878-1 | − | 328 | 411 | 967 | 1706 |
| 20 | 277-6-3-1 | 878-2 | + | 2037 | 1260 | 6251 | 9547 |
| 21 | 277-6-3-1 | 879-1 | + | 1739 | 1336 | 9560 | 12634 |
| 22 | 277-6-3-1 | 880-1 | + | 1261 | 1070 | 8310 | 10641 |
| 23 | 277-6-3-1 | 880-2 | ND* | 1771 | 1185 | 6538 | 9495 |
| 24 | 277-6-3-2 | 881-1 | + | 1882 | 1223 | 9360 | 12466 |
| 25 | 277-6-3-2 | 881-2 | + | 3507 | 1256 | 5587 | 10350 |
| 26 | 277-6-3-2 | 882-1 | + | 667 | 757 | 5922 | 7346 |
| 27 | 277-6-3-2 | 882-2 | + | 638 | 793 | 7394 | 8825 |
| 28 | 277-6-3-2 | 883-1 | + | 1496 | 937 | 5048 | 7480 |
| 29 | 277-6-3-2 | 884-1 | + | 1254 | 1072 | 6231 | 8557 |
| 30 | 277-6-3-2 | 884-2 | + | 1049 | 815 | 6527 | 8391 |
| 31 | 277-6-3-2 | 884-3 | ND* | 1172 | 983 | 7114 | 9868 |
| 32 | 277-6-3-3 | 885-1 | + | 530 | 759 | 6751 | 8041 |
| 33 | 277-6-3-3 | 885-2 | − | 255 | 216 | 973 | 1443 |
| 34 | 277-6-3-3 | 885-3 | ND* | 931 | 963 | 8721 | 10616 |
| 35 | 277-6-3-3 | 886-1 | + | 1490 | 1067 | 8242 | 10799 |
| 36 | 277-6-3-3 | 887-1 | − | 263 | 279 | 791 | 1333 |
| 37 | 277-6-3-3 | 887-2 | − | 251 | 251 | 722 | 1224 |
| 38 | 277-6-3-3 | 887-3 | ND* | 1666 | 877 | 5945 | 8488 |
| 39 | 277-6-3-3 | 888-1 | + | 467 | 575 | 4439 | 5481 |

*ND, not determined.

In summary, the expression of the CRC chimeric construct in conjunction with flavanone 3-hydroxylase cosuppression results in transformants that accumulate up to four times higher amounts of isoflavones when compared to wild type soybean while retaining the wild type profile of the individual isoflavone components. The isoflavone levels seen in these transgenic plants are higher than any wild type soybean cultivar known to date.

What is claimed is:

1. A method of increasing isoflavonoid production in an isoflavonoid-producing plant, the method comprising:
   a) transforming a plant with
      (1) a first recombinant DNA construct comprising a polynucleotide selected from the group consisting of:
         (i) a polynucleotide encoding all or part of a flavanone 3-hydroxylase from the plant;
         (ii) a polynucleotide comprising a 5' non-coding sequence, a 3' non-coding sequence, or both, of an isolated nucleic acid fragment which encodes a flavanone 3-hydroxylase from the plant; or
         (iii) a polynucleotide comprising (i) and (ii); and
      (2) at least one second recombinant DNA construct comprising a polynucleotide encoding a *maize* C1 myb transcription factor and a *maize* R myc-type transcription factor; and
   b) growing the transformed plant of (a); and
   c) evaluating the plant or plant part obtained from the transformed plant for an increased quantity of isoflavonoid in the transformed plant or plant part as compared to the plant or plant parts obtained from an untransformed plant.

2. The method of claim 1 wherein the first recombinant DNA construct further comprises a polynucleotide encoding all or part of a flavanone 3-hydroxylase from the plant operably linked in a sense orientation to a promoter.

3. The method of claim 1 wherein the first recombinant DNA construct further comprises a polynucleotide encoding all or part of a flavanone 3-hydroxylase from the plant operably linked in an anti-sense orientation to a promoter.

4. The method of claim 2 or claim 3 wherein the first recombinant DNA construct comprises a stem-loop structure selected from the group consisting of: (1) a structure wherein the loop comprises the polynucleotide encoding all or part of a flavanone 3-hydroxylase from the plant, and (2) a structure wherein the stem comprises the polynucleotide encoding all or part of a flavanone 3-hydroxylase from the plant.

5. The method of claim 1 wherein the plant is transformed with a first recombinant DNA construct comprising a nucleotide sequence encoding all or part of a flavanone 3-hydroxylase from the plant, a second recombinant DNA construct comprising a nucleotide sequence encoding a *maize* C1 myb transcription factor, and a third recombinant DNA construct comprising a nucleotide sequence encoding a *maize* R myc-type transcription factor.

6. The method of claim 1 wherein the first recombinant DNA construct and the second recombinant DNA construct form one recombinant expression vector.

7. The method of claim 1 wherein the first recombinant DNA construct further comprises a seed-specific promoter.

8. The method of claim 1 wherein the isoflavonoid-producing plant is selected from the group consisting of soybean, clover, mung bean, lentil, hairy vetch, alfalfa, lupine, sugar beet, and snow pea.

9. An isoflavonoid-producing plant made by the method of claim 1, claim 2, claim 3, claim 4, claim 5. Claim 6, or claim 7, wherein the plant has an increased quantity of isoflavonoid as compared with an untransformed plant.

10. The isoflavonoid-producing plant of claim 9 wherein the plant is selected from the group consisting of soybean, clover, mung bean, lentil, hairy vetch, alfalfa, lupine, sugar beet, and snow pea.

11. Seeds or plant parts of the plant of claim 10, wherein the seed or the plant parts comprise the recombinant DNA constructs.

12. An isoflavonoid-producing plant comprising in its genome (1) a first recombinant DNA construct comprising a polynucleotide selected from the group consisting of:
   i) a pal ynudeotide encoding all or part of a flavanone 3-hydroxylase from the plant;
   (ii) a polynucleotide comprising 5' non-coding sequence, 3' non-coding sequence, or both, of an isolated nucleic acid fragment which encodes a flavanone 3-hydroxylase from the plant; or
   (iii) a polynucleotide comprising (i) and (ii); and
(2) at least one second recombinant DNA construct comprising a polynucleotide encoding a *maize* C1 myb transcription factor and a *maize* R myc-type transcription factor;

wherein the plant or plant parts obtained from the transformed plant have an increased quantity of isoflavonold as compared to the plant or plant parts obtained from an untransformed plant.

13. The Isoflavonold-producing plant of claim 12 wherein the plant is selected from the group consisting of soybean, clover, mung bean, lentil, hairy vetch, alfalfa, lupine, sugar beet, and snow pea.

14. Seeds or plant parts of the plant of claim 13 wherein the seed or the plant parts comprise the recombinant DNA constructs.

15. The method of claim 1 wherein the plant is transformed with said first recombinant DNA construct comprising a nucleotide sequence encoding all or part of a flavanone 3-hydroxylase from the plant and said second recombinant DNA construct comprising a nucleotide sequence, encoding a chimeric transcription factor, comprising the *maize* R coding region situated between the coding regions of a *maize* C1 DNA-binding domain and the *maize* C1 activation domain.

16. The isoflavonoid-producing plant of claim 12 wherein the plant comprises said first recombinant DNA construct comprising a nucleotide sequence encoding all or part of a flavanone 3-hydroxylase from the plant and said second recombinant DNA construct comprising a nucleotide sequence, encoding a chimeric transcription factor, comprising the *maize* R coding region situated between the coding regions of the *maize* C1 DNA-binding domain and the *maize* C1 activation domain.

* * * * *

UNITED STATES PATENT AND TRADEMARK OFFICE
CERTIFICATE OF CORRECTION

PATENT NO.         : 7,189,895 B2                                    Page 1 of 1
APPLICATION NO. : 10/459159
DATED              : March 13, 2007
INVENTOR(S)        : Brian McGonigle and Joan T. Odell It is certified that error appears in the above-identified patent and that said Letters Patent is hereby corrected as shown below:

Last page of patent, Claims section Col. 38, Claim 12(1)(i) Line 3 - delete "pal ynudeotide" and insert therefor --polynucleotide--.

Last page of patent, Claims section Col. 38, Claim 13 Line 18 - delete "Isoflavonold" and insert therefor --isoflavonoid--.

Signed and Sealed this

Fourth Day of December, 2007

JON W. DUDAS
*Director of the United States Patent and Trademark Office*